(12) United States Patent
Chen et al.

(10) Patent No.: US 7,700,287 B2
(45) Date of Patent: Apr. 20, 2010

(54) COMPOSITIONS AND METHODS FOR TERMINATING A SEQUENCING REACTION AT A SPECIFIC LOCATION IN A TARGET DNA TEMPLATE

(75) Inventors: Shiaw-Min Chen, Fremont, CA (US); John W. Brandis, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 208 days.

(21) Appl. No.: 11/341,321

(22) Filed: Jan. 27, 2006

(65) Prior Publication Data

US 2006/0172333 A1 Aug. 3, 2006

Related U.S. Application Data

(60) Provisional application No. 60/647,277, filed on Jan. 28, 2005, provisional application No. 60/722,222, filed on Sep. 30, 2005.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.31; 536/24.32; 536/24.33

(58) Field of Classification Search ............ 435/6, 435/91.2; 536/24.31, 24.32, 24.33
See application file for complete search history.

(56) References Cited

U.S. PATENT DOCUMENTS 6,180,338 B1 * 1/2001 Adams .................... 435/6
6,361,942 B1 3/2002 Coull et al.
6,420,115 B1 7/2002 Erikson et al.
6,432,642 B1 8/2002 Livak et al.

FOREIGN PATENT DOCUMENTS

| WO | WO 94/17207 A | 4/1994 |
| WO | WO 9417207 A1 * | 8/1994 |
| WO | WO 03/035671 A | 5/2003 |
| WO | WO 2005/093101 A1 | 10/2005 |

OTHER PUBLICATIONS

Esposito D, et al. Blocking oligonucleotides improve sequencing through inverted repeats. Biotechniques, vol. 35(5), pp. 914-916,918, 920, Nov. 2003.*
Takiya T et al. RApid selection of nonhotspot mutants among hisD+ revertants of *Salmonella typhimurium* TA98 in Ames test by peptide nucleic acid (PNA)-mediated PCR clamping. J Bioscience and Bioengineering, vol. 96, No. 6, pp. 588-590, 2003.*
Giddings, Michael C. et al., "A Software System for Data Analysis in Automated DNA Sequencing," *Genome Research*, Jun. 1998, vol. 8, No. 6, pp. 644-665, Cold Spring Harbor Laboratory Press, Woodbury, NY, US.
Sanger, P. et al., "DNA Sequencing With Chain-Terminating Inhibitors," *Proc. Natl. Acad. Sci.*, USA, Dec. 1977, vol. 74, No. 12, pp. 5463-5467, New York, NY, US.
Int'l Search Report and Written Opinion of the Int'l Searching Authority for PCT/US2006/002941.

* cited by examiner

*Primary Examiner*—Suryaprabha Chunduru

(57) ABSTRACT

Compositions and methods for sequencing a template polynucleotide comprising a sequence of interest are provided herein. The compositions and methods employ at least one blocking probe that is designed to bind in a sequence-specific manner to a blocking sequence such that primer extension beyond the site where the blocking probe binds is reduced or prevented.

12 Claims, 11 Drawing Sheets

SEQUENCE LISTING

<160> NUMBER OF SEQ ID NOS: 10

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aataaactgc agaacc                                                    16

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgcagaacc aatgcag                                                   17

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcagaaccaa tgcagg                                                    16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agaaccaatg caggtc                                                    16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaactgcaga accaat                                                    16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base

```
<222> LOCATION: (9)
<223> OTHER INFORMATION: Diaminopurine
<220> FEATURE:
<221> NAME/KEY: modified_base
<222> LOCATION: (14)
<223> OTHER INFORMATION: Diaminopurine

<400> SEQUENCE: 6
ggttctgcng tttntt                                                        16

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (5)
<223> OTHER INFORMATION: Diaminopurine
<220> FEATURE:
<221> NAME/KEY: modified_base
<222> LOCATION: (16)
<223> OTHER INFORMATION: Diaminopurine

<400> SEQUENCE: 7
ctgcnttggt tctgcng                                                       17

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (6)
<223> OTHER INFORMATION: Diaminopurine

<400> SEQUENCE: 8
cctgcnttgg ttgtgc                                                        16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (2)
<223> OTHER INFORMATION: Diaminopurine
<220> FEATURE:
<221> NAME/KEY: modified_base
<222> LOCATION: (8)
<223> OTHER INFORMATION: Diaminopurine

<400> SEQUENCE: 9
gncctgcntt ggttct                                                        16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
```

-continued

```
<221> NAME/KEY: modified_base
<222> LOCATION: (1)
<223> OTHER INFORMATION: Diaminopurine
<220> FEATURE:
<221> NAME/KEY: modified_base
<222> LOCATION: (12)
<223> OTHER INFORMATION: Diaminopurine

<400> SEQUENCE: 10
nttggttctg cngttt                                              16
```

COMPOSITIONS AND METHODS FOR TERMINATING A SEQUENCING REACTION AT A SPECIFIC LOCATION IN A TARGET DNA TEMPLATE

1. CROSS REFERENCE TO RELATED APPLICATIONS

This application claims benefit under 35 U.S.C. § 119(e) to application Ser. No. 60/647,277, filed Jan. 28, 2005 and to application Ser. No. 60/722,222, filed Sep. 30, 2005, the contents of which are incorporated herein by reference.

2. BACKGROUND

Polynucleotide sequencing is a fundamental technology in molecular biology and life sciences in general. Dideoxy sequencing (Sanger et al., 1997, Proc. Nat. Acad. Sci. 74:5463) involves the generation of four populations of single-stranded DNA fragments, having one defined terminus and one variable terminus. Dideoxy sequencing is an enzymatic chain termination method in which four base specific sets of DNA fragments are formed by starting with a primer/template system, elongating the primer into the unknown DNA sequence area, thereby copying the template and synthesizing a complementary strand by a polymerase. In some embodiments, four separate reactions are terminated, each reaction being caused to terminate at a specific base (G, A, T or C) via incorporation of the appropriate chain terminating nucleotide. The four different sets of fragments are each separated on the basis of their length, such as on a high resolution polyacrylamide gel; each band on the gel corresponds colinearly to a specific nucleotide in the DNA sequence, thus identifying the positions in the sequence of the given nucleotide base. Capillary electrophoresis (CE) is another method used to separate single-stranded DNA sequencing fragments (see, e.g., U.S. Pat. No. 5,374,527); each intensity peak on an electropherogram ideally corresponds colinearly to a specific nucleotide in the DNA sequence

3. SUMMARY

Provided herein are compositions and methods useful for sequencing a polynucleotide of interest. The compositions and methods described herein employ a polynucleotide template comprising a sequence of interest, one or more blocking probes, a sequencing primer, a polymerase, nucleoside triphosphates, terminators, and an optional detectable label. The blocking probe can be designed to bind to a blocking sequence present on a polynucleotide template such that primer extension beyond the site where the blocking probe binds is reduced or prevented. Thus, by including a blocking probe in the sequencing reaction, a population of primer extension products can be generated in which all of the products comprise all, or a portion thereof, of the sequence of interest.

Including a blocking probe in the sequencing reaction is also useful for generating primer extension products within a given size range. For example, if primer extension products ranging from 80 to 500 base pairs are optimum for a given separation/detection system, the blocking probe can be designed to bind to the polynucleotide template such that the longest primer extension product does not exceed 500 base pairs.

Blocking probes useful in the compositions and methods described herein include, but are not limited to, oligonucleotides, oligonucleotide analogs, oligonucleotide mimics such as PNA and chimeric oligonucleotides, as defined above. In some embodiments, the blocking probe is PNA. In other embodiments, the blocking probe can be an oligonucleotide with a blocked 3' end. The 3' end can be blocked with any moiety that is not a suitable substrate for polymerase-mediated extension, such as a phosphate moiety or a terminator, or with a moiety that does not hybridize to the polynucleotide template.

The length of the blocking probe depends, in part, on the base composition. For example, in embodiments in which the blocking probe comprises PNA, the blocking probe can be between 10 to 20 nucleobases in length. In embodiments in which the blocking probe comprises an oligonucleotide or oligonucleotide analog, the blocking probe can be between 15 to 100 nucleobases in length. In other embodiments, the blocking probe can be greater than 100 nucleobases in length.

To reduce or block primer extension beyond the sequence of interest, the blocking probe should bind to the template polynucleotide before the polymerase used to generate the primer extension products begins to extend the primer. For example, the blocking probe can remain bound to the polynucleotide template throughout the various temperatures used to anneal, extend, and denature the primer. In another specific example, the blocking probe can re-anneal to the polynucleotide template prior to the initiation of the primer extension step. Thus, the melting point temperature ($T_m$) of the blocking probe should be greater than the temperature at which the polymerase used to generate the primer extension products begins to extend the primer. In some embodiments, the $T_m$ of the blocking probe can be between 1° C. to 20° C. greater than the temperature at which the polymerase used to generate the primer extension products begins to extend the primer. For example, if the polymerase used in the sequencing reactions is active at 96° C., than the $T_m$ of the blocking probe can range between 97° C. to 110° C. In another example of the embodiments described herein, if the polymerase used in the sequencing reactions is active at 80° C., than the $T_m$ of the blocking probe can range between 90° C. to 100° C.

In other embodiments, the $T_m$ of the blocking probe can be lower than the temperature at which the polymerase used in the sequencing reactions begins to extend the primer, provided that the $T_m$ of the blocking probe is greater than the $T_m$ of the sequencing probe.

It is not essential to the methods described herein that the blocking probe be designed to bind only to sequence(s) present in the polynucleotide template that are not present in the sequence of interest. The sequence of the blocking probe can comprise any combination of bases capable of binding to sequences comprising the polynucleotide template and/or the sequence of interest, as long as hybridization of the blocking probe to the polynucleotide template reduces or blocks primer extension beyond the site where the blocking probe binds. For example, the sequence of the blocking probe can be designed to hybridize to a sequence of nucleotides that is present in the polynucleotide template, but not in the sequence of interest. In other embodiments, the sequence of the blocking probe can include one or more bases that are capable of binding to the sequence of interest. In embodiments in which the blocking probe binds the sequence of interest, the extent of binding between the blocking probe and the sequence of interest should not interfere with the generation of primer extension products from the sequence of interest.

Typically, the blocking probe is not a template for primer extension, e.g., the blocking probe should be non-extendible. However, in some embodiments, the blocking probe can be extendible, provided that the extension products so generated do not interfere with the sequencing reaction.

In some embodiments, the sequence of the blocking probe is designed to hybridize to a sequence of nucleotides that is present in vectors commonly used to provide nucleic acid templates for sequencing reactions. For example, "universal" blocking probes can be designed that bind to one side or the other of cloning sites in plasmid, phagemid, bacteriophage λ, and bacteriophage M13 vectors. In other embodiments, the blocking probe can be designed to hybridize to a nucleic acid sequence that is not present in vectors commonly used for sequencing. For example, a blocking probe complementary to a random sequence of nucleotides can be designed using commercially available computer programs developed for the design, selection and placement of nucleobase oligomers used as probes or primers.

The blocking probe can be designed to hybridize to a region of the polynucleotide that is adjacent to the 5'-terminus of the sequence of interest. In some embodiments, the blocking probe hybridizes to a region of the polynucleotide that is immediately adjacent to the sequence of interest. In other embodiments, the blocking probe is designed to hybridize to a region of the polynucleotide that is separated by one or more bases from the 5' terminus of the sequence of interest. For example, 1, 5, 10, 15, or 20 bases can separate the region of the polynucleotide to which the blocking probe binds from the 5' terminus of the sequence of interest.

Different combinations of blocking probes can be used in the reaction mixtures described herein. For example, in some embodiments, each reaction mixture comprises a single blocking probe. In other embodiments, one or more of the reaction mixtures can comprise two or more blocking probes. In embodiments comprising two or more blocking probes, the sequences of the blocking probes can be the same or they can differ. For example, a reaction mixture can comprise two blocking probes with the same sequence. As another example, a reaction mixture can comprise two blocking probes, wherein each probe, independently of the other, comprises a different sequence. As another specific example, two or more reaction mixtures can be set up, wherein each reaction mixture, independently of the other, can comprise one or more blocking probes having the same sequence or different sequences.

Oligonucleotide primers useful in the compositions and methods described herein should have a free 3'-hydroxyl group to allow chain extension by the polymerase, be complementary to a region of the sequence of interest, and be sufficiently long to hybridize to form a stable duplex. In some embodiments, the sequencing primer comprises a detectable label. Commercially available oligonucleotide primers commonly used in Sanger-type sequencing reactions can be used in the compositions and methods described herein. In other embodiments, synthetic oligonucleotide primers designed to hybridize to a specific priming sequence can be used in the methods and compositions described herein.

The polynucleotide template comprising the sequence of interest can be provided from any source. For example, the polynucleotide template can comprise a vector commonly used for sequencing reactions, and a cloned insert comprising the sequence of interest. In some embodiments, the polynucleotide template can be an amplicon generated from an amplification reaction. In addition to the sequence of interest, the amplicon can comprise a sequence complementary to a sequencing primer and/or a sequence complementary to a blocking probe.

The compositions and methods described herein find use in nucleic acid sequencing reactions that involve an extension/termination reaction using an oligonucleotide primer. Primed synthesis is carried out in the presence of a terminator to generate a plurality of differently sized primer extension products. The resulting primer extension products can be separated based upon their size, and the sequence of the sequence of interest determined therefrom. In some embodiments, capillary electrophoresis can be used to separate the primer extension products. In some embodiments, multiple nucleic acid samples can be sequenced using a capillary electrophoresis method that does not use a reconditioning step to remove traces of the preceding sample and/or contaminants.

To improve detection of the differently sized primer extension products, various labeling strategies using a detectable label can be employed. For example, the detectable label may be attached to the sequencing primer, the nucleoside triphosphates, or the terminators. In some embodiments, the detectable label is attached to the sequencing primer and four separate sequencing reactions comprising a blocking probe, the labeled sequencing primer, and the appropriate terminators are used to produce a plurality of oligonucleotide fragments of varying lengths. In these embodiments, the fragments produced in the four sequencing reactions are analyzed separately and the sequence of interest determined. The detectable label may be any label that is operative in accordance with the various compositions and methods described herein. In some embodiments, the detectable label comprises a fluorescent entity. In other embodiments, the detectable label comprises a radioactive entity.

In some embodiments, the detectable label is attached to one or more nucleoside triphosphates in each of four separate sequencing reactions comprising a blocking probe, the sequencing primer, and the appropriate terminator. In these embodiments, the fragments produced in the four different sequencing reactions are analyzed separately and the sequence of interest determined. The detectable label may be any label that is operative in accordance with the various compositions and methods described herein. In some embodiments, the detectable label comprises a fluorescent entity. In other embodiments, the detectable label comprises a radioactive entity.

In some embodiments, the detectable label is attached to the terminators. The terminators can comprise the same detectable label, or different, spectrally resolvable detectable labels. In embodiments in which the detectable label attached to the terminators is the same, four separate sequencing reactions are used. Each reaction, independently of the others, comprises a blocking probe, a sequencing primer and a terminator complementary to adenosine, cytosine, guanosine, thymidine or uridine are used to produce a plurality of oligonucleotide fragments of varying lengths. The fragments produced in the four different sequencing reactions are analyzed separately and the sequence of the sequence of interest determined. The detectable label may be any label that is operative in accordance with the various compositions and methods described herein. In some embodiments, the detectable label comprises a fluorescent entity.

In other embodiments, the terminators comprise different, spectrally resolvable detectable labels. In these embodiments, a single sequencing reaction mixture comprising the blocking probe, the sequencing primer and a labeled terminator complementary to adenosine, cytosine, guanosine, thymidine or uridine is used to produce a plurality of oligonucleotide fragments of varying lengths. The fragments produced in the sequencing reaction are analyzed and the sequence of interest determined. The detectable label may be any label that is operative in accordance with the various compositions and methods described herein. In some embodiments, the detectable label comprises a fluorescent entity.

Also provided are compositions and kits useful for carrying out the various methods described herein. In some embodiments, the kits comprise a blocking probe. Additionally, the kits can comprise a mixture of different terminating nucleotides, each of which comprises a detectable label. In other embodiments, the kits can comprise a blocking probe, a mixture of different terminating nucleotides, each of which comprises a detectable label, nucleoside triphosphates and a polymerase.

In yet other embodiments, the kits can comprise a vector that can be used to provide a nucleic acid template for the sequencing reactions. The vector can comprise one or more restriction enzyme sites for the insertion of a sequence of insert, as well as sequences capable of hybridizing with a blocking probe and/or with a sequencing primer.

4. BRIEF DESCRIPTION OF THE DRAWINGS

The skilled artisan will understand that the drawings, described below, are for illustration purposes only. The drawings are not intended to limit the scope of the present teachings in any way.

Figure 7:
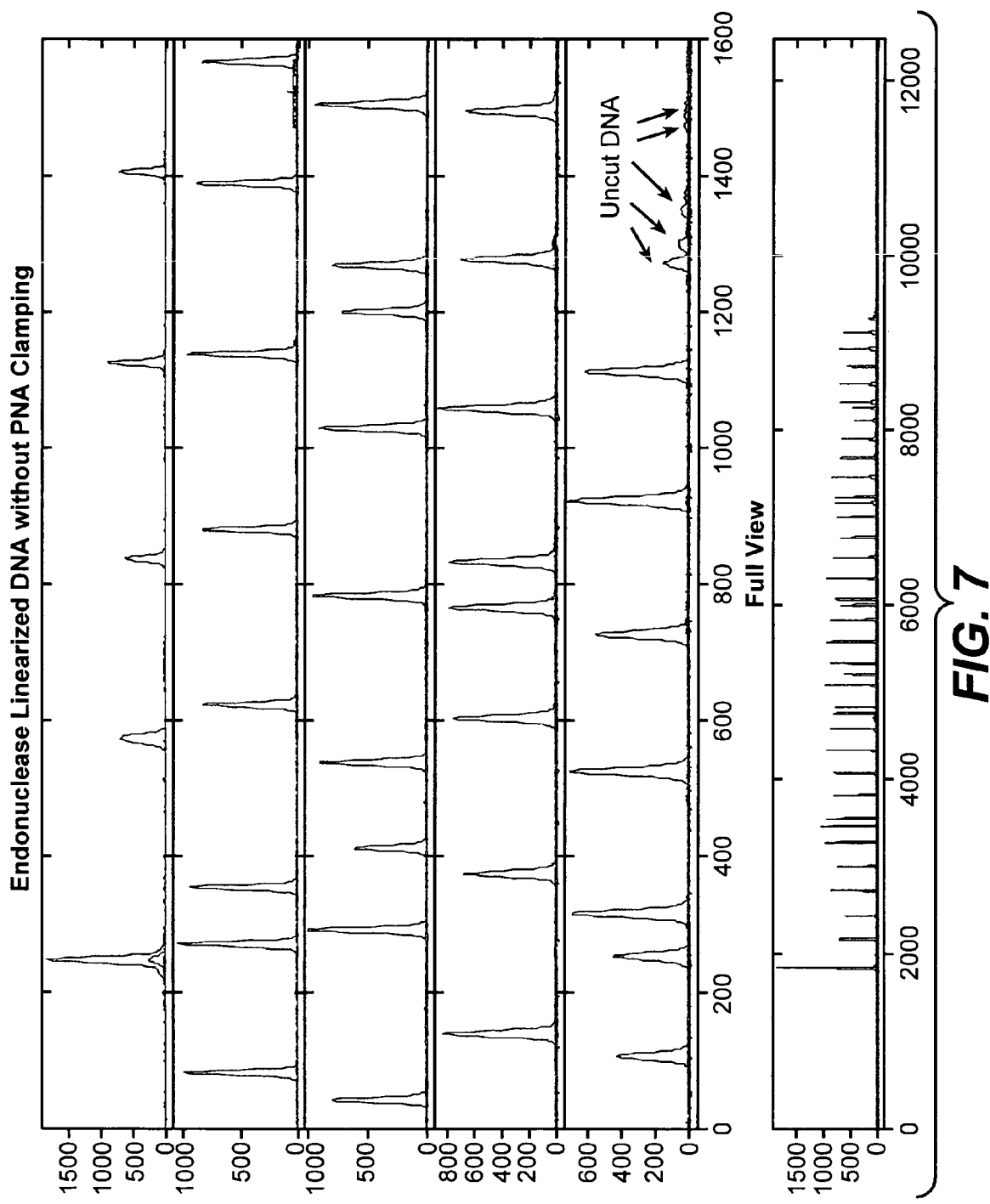
Figure 8:
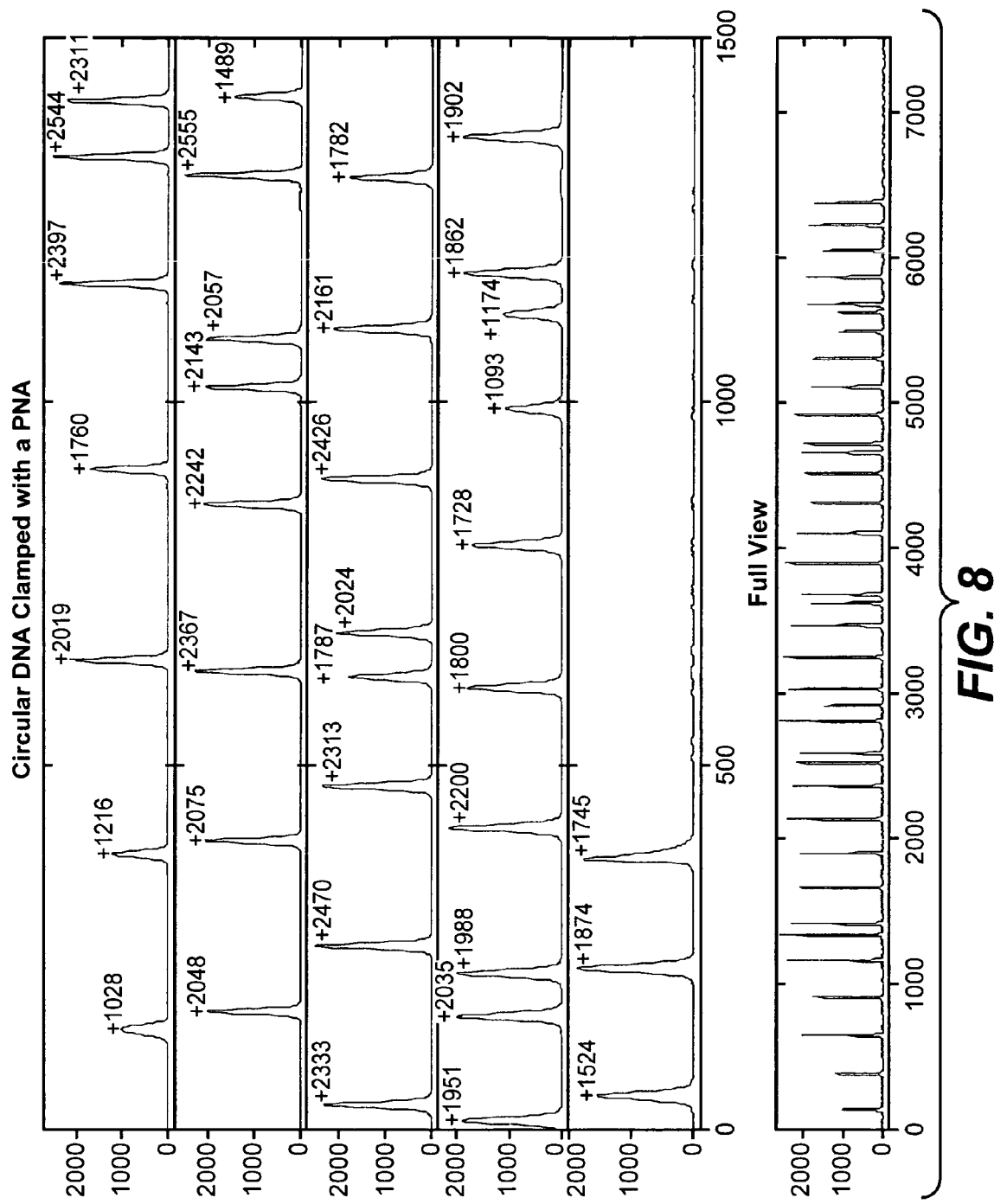
Figure 9A:
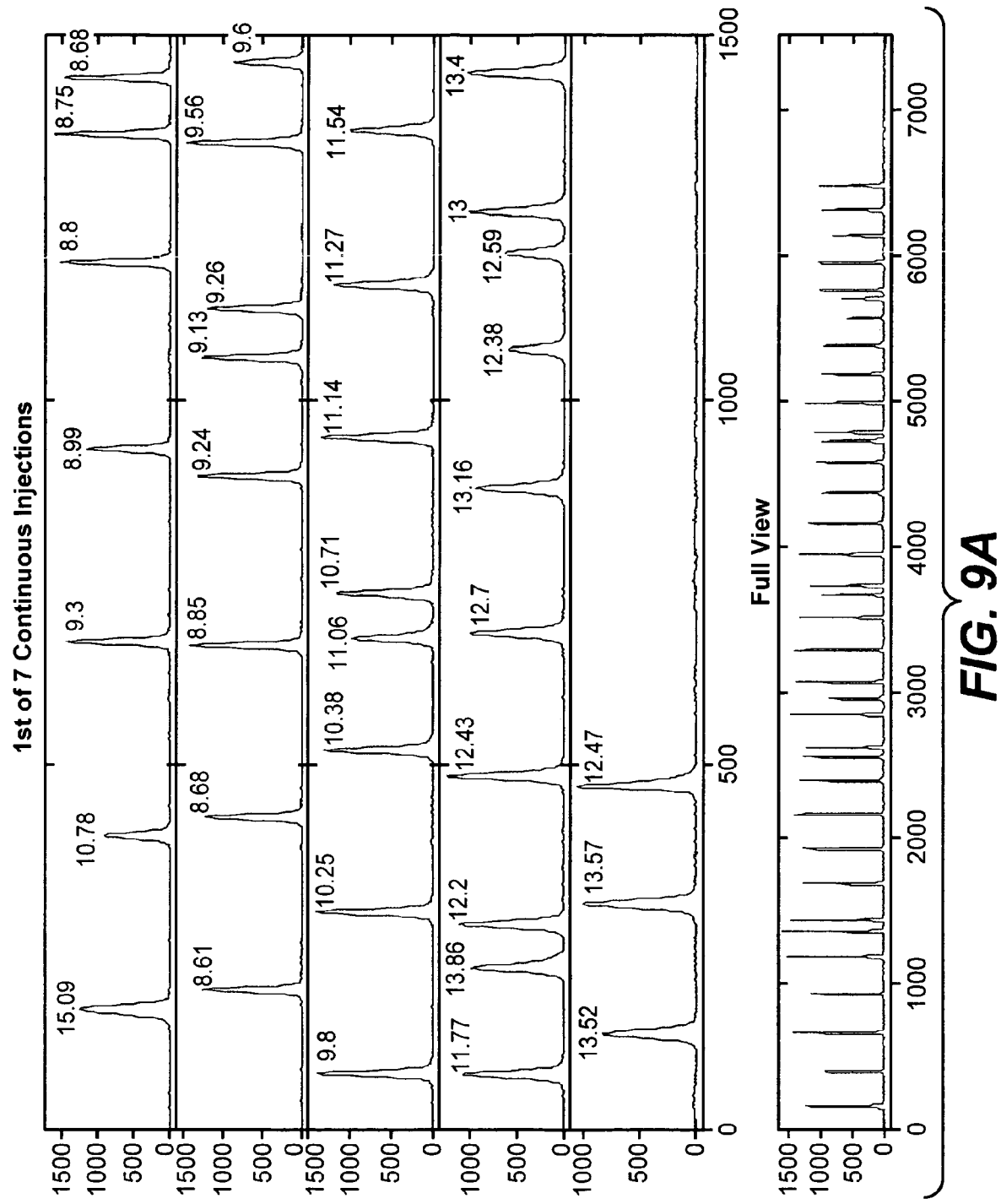
Figure 9B:
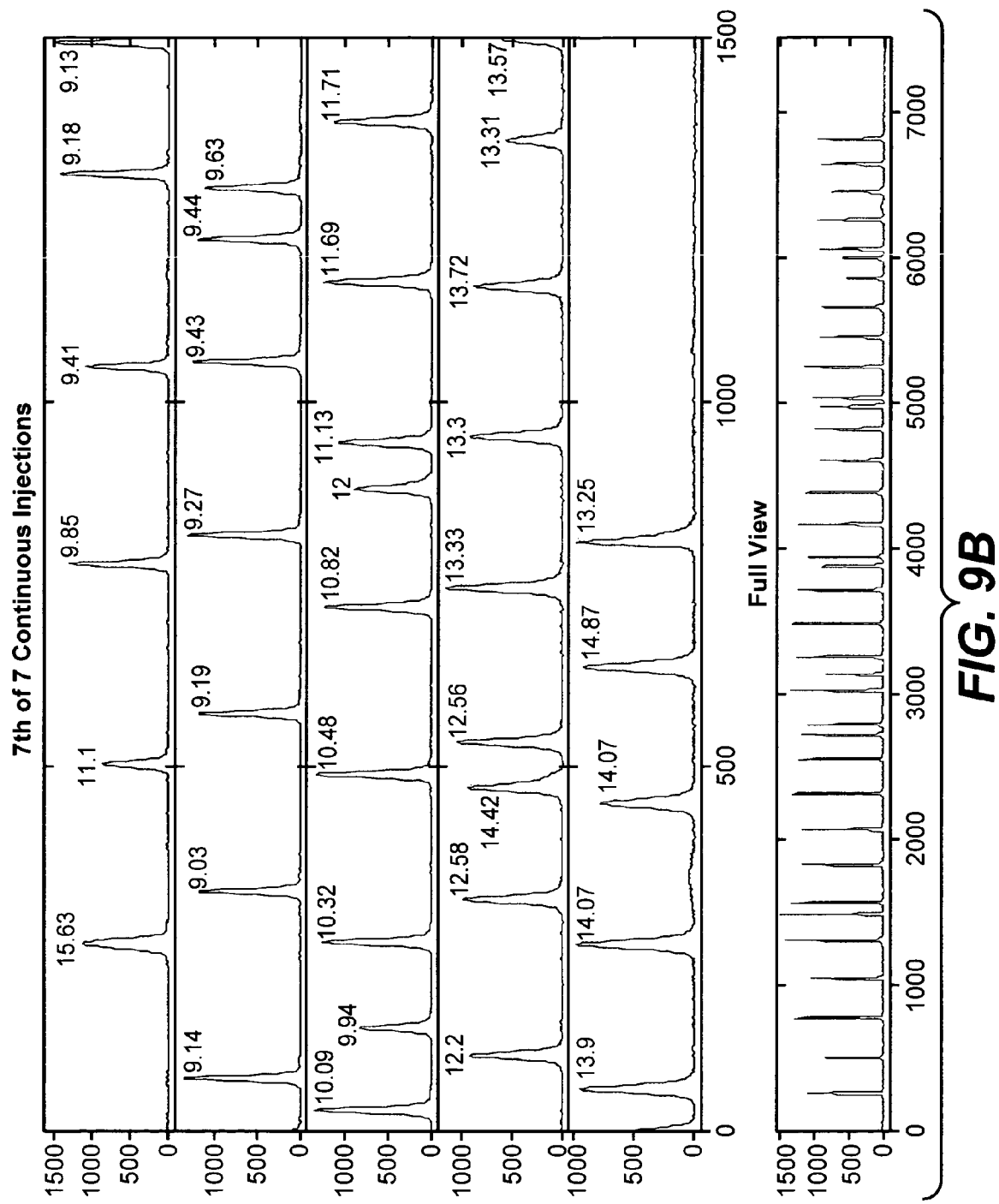
Figure 10:
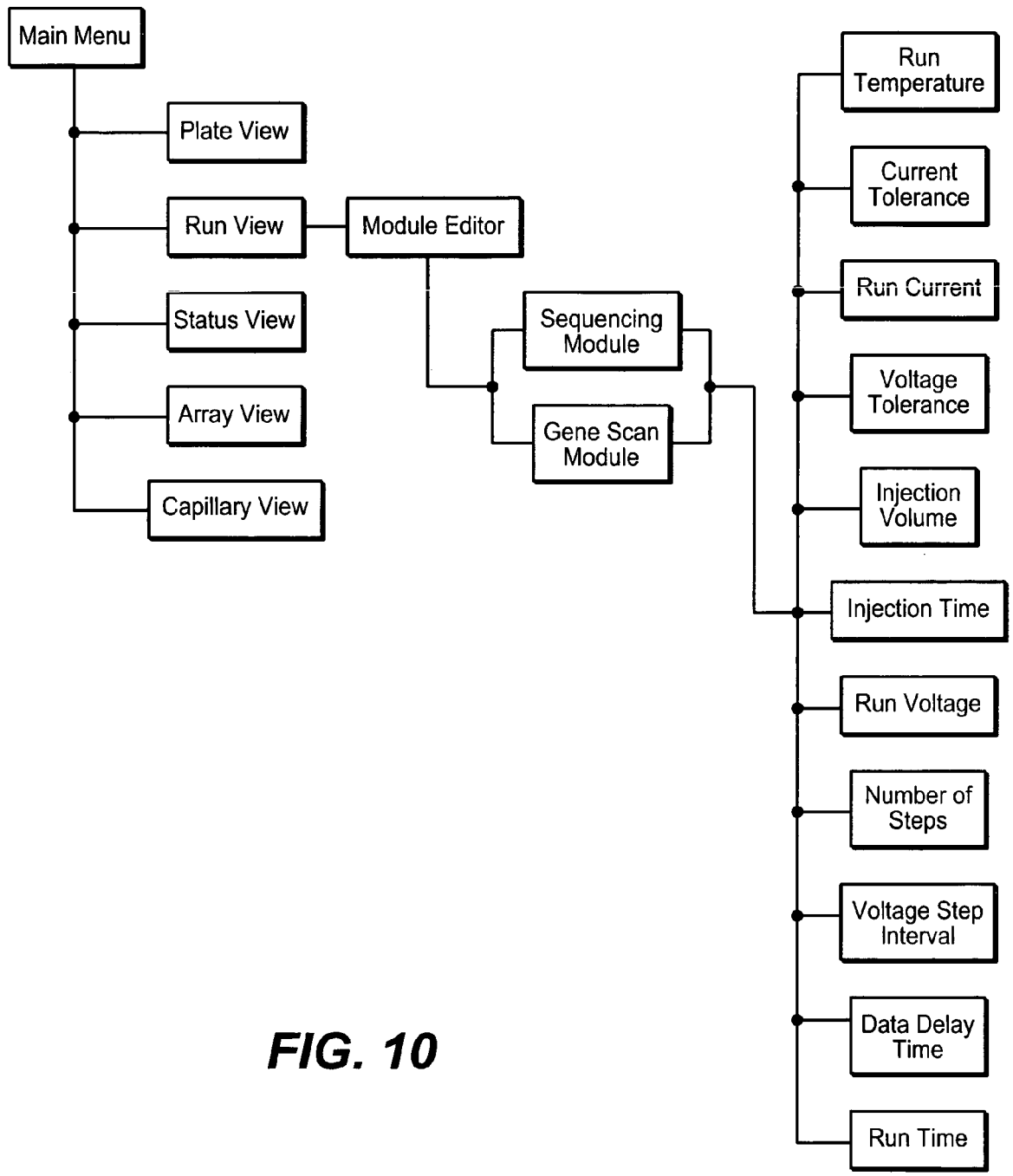

FIGS. 6A-6D schematically illustrate some embodiments of a sequencing vector;

FIG. 7 illustrates the presence of run-on products from a sequencing reaction that did not include a blocking probe;

FIG. 8 depicts an embodiment of the method in which a blocking probe was included in the sequencing reaction;

FIGS. 9A-9B depict an embodiment of the method in which 1 to 7 samples are sequentially injected in a silica capillary tube dynamically coated with a polymer; and FIG. 10 depicts a main menu, including the module editor, for a capillary electrophoresis data collection software program.

5. DETAILED DESCRIPTION

It is to be understood that both the foregoing general description and the following detailed description are exemplary and explanatory only and are not restrictive of the embodiments described herein. In this application, the use of the singular includes the plural unless specifically stated otherwise. Also, the use of "or" means "and/or" unless stated otherwise. Similarly, "comprise," "comprises," "comprising," "include," "includes" and "including" are not intended to be limiting.

The abbreviations used throughout the specification and in the FIGS. to refer to sequences of interest, blocking sequences, sequences complementary to the sequencing primers, polynucleotides, blocking probes, sequencing primers, deoxynucleotides, and terminators comprising specific nucleobase sequences are the conventional one-letter abbreviations. Capital letters represent nucleotide sequences (e.g., RNA and DNA sequences) and lower case letters represent nucleotide mimic sequences (e.g., PNA sequences). Thus, when included in a poly or oligonucleotide, the naturally occurring encoding nucleobases are abbreviated as follows: adenine (A), guanine (G), cytosine (C), thymine (T), and uracil (U). When included in a poly or oligonucleotide mimic, such as PNA, the naturally occurring encoding nucleobases are abbreviated as follows: adenine (a), guanine (g), cytosine (c), thymine (t), and uracil (u). "Nucleobase sequence" or "sequence" are used interchangeably.

Also, unless specified otherwise, poly or oligonucleotide sequences that are represented as a series of one-letter abbreviations are presented in the 5'→3' direction, in accordance with common convention. Poly or oligonucleotide mimic sequences that have amino and carboxy termini, such as PNAs, are presented in the amino-to-carboxy direction, in accordance with common convention. For the purposes of distinguishing parallel from anti-parallel hybridization orientation, it is understood that the 5' terminus of an oligonucleotide corresponds to the amino terminus of a PNA and the 3' terminus of an oligonucleotide corresponds to the carboxy terminus of a PNA.

5.1 Definitions

As used herein, the following terms and phrases are intended to have the following meanings:

"Nucleobase" or "base" means those naturally occurring and those synthetic heterocyclic moieties commonly known to those who utilize nucleic acid or polynucleotide technology or utilize polyamide or peptide nucleic acid technology to thereby generate polymers that can hybridize to polynucleotides in a sequence-specific manner. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deazaguanine), N9-(7-deaza-8-aza-guanine) and N8-(7-deaza-8-aza-adenine). Other non-limiting examples of suitable nucleobases include those nucleobases illustrated in FIGS. 2(A) and 2(B) of Buchardt et al. (WO 92/20702 or WO 92/20703).

"Nucleobase Polymer or Oligomer" refers to two or more nucleobases that are connected by linkages that permit the resultant nucleobase polymer or oligomer to hybridize to a polynucleotide having a complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide or peptide nucleic acids. Nucleobase polymers or oligomers can vary in size from a few nucleobases, from 2 to 40 nucleobases, to several hundred nucleobases, to several thousand nucleobases, or more.

"Polynucleotides or Oligonucleotides" refer to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof.

"Polynucleotide or Oligonucleotide Analog" refers to nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. No. 6,013,785 and U.S. Pat. No. 5,696,253 (see also, Dagani 1995, Chem. & Eng. News 4-5:1153; Dempey et al., 1995, J. Am. Chem. Soc. 117:6140-6141). Such positively charged analogues in which the sugar is 2'-deoxyribose are referred to as "DNGs," whereas those in which the sugar a ribose are referred to as "RNGs." Specifically included within the definition of poly- and oligonucleotide analogs are locked nucleic acids (LNAs; see, e.g. Elayadi et al., 2002, Biochemistry 41:9973-9981; Koshkin et al., 1998, J. Am. Chem. Soc. 120: 13252-3; Koshkin et al., 1998, Tetrahedron Letters, 39:4381-4384; Jumar et al., 1998, Bioorganic & Medicinal Chemistry Letters 8:2219-2222; Singh and Wengel, 1998, Chem. Commun., 12:1247-1248; WO 00/56746; WO 02/28875; and, WO 01/48190; all of which are incorporated herein by reference in their entireties).

"Polynucleotide or Oligonucleotide Mimic" refers to a nucleobase polymer or oligomer in which one or more of the backbone sugar-phosphate linkages is replaced with a sugar-phosphate analog. Such mimics are capable of hybridizing to complementary polynucleotides or oligonucleotides, or polynucleotide or oligonucleotide analogs or to other polynucleotide or oligonucleotide mimics, and may include backbones comprising one or more of the following linkages: positively charged polyamide backbone with alkylamine side chains as described in U.S. Pat. No. 5,786,461; U.S. Pat. No. 5,766,855; U.S. Pat. No. 5,719,262; U.S. Pat. No. 5,539,082 and WO 98/03542 (see also, Haaima et al., 1996, Angewandte Chemie Int'l Ed. in English 35:1939-1942; Lesnick et al., 1997, Nucleosid. Nucleotid. 16:1775-1779; D'Costa et al., 1999, Org. Lett. 1:1513-1516 see also Nielsen, 1999, Curr. Opin. Biotechnol. 10:71-75); uncharged polyamide backbones as described in WO 92/20702 and U.S. Pat. No. 5,539,082; uncharged morpholino-phosphoramidate backbones as described in U.S. Pat. No. 5,698,685, U.S. Pat. No. 5,470,974, U.S. Pat. No. 5,378,841 and U.S. Pat. No. 5,185,144 (see also, Wages et al., 1997, BioTechniques 23:1116-1121); peptide-based nucleic acid mimic backbones (see, e.g., U.S. Pat. No. 5,698,685); carbamate backbones (see, e.g., Stirchak & Summerton, 1987, J. Org. Chem. 52:4202); amide backbones (see, e.g., Lebreton, 1994, Synlett. February, 1994:137); methylhydroxyl amine backbones (see, e.g., Vasseur et al., 1992, J. Am. Chem. Soc. 114:4006); 3'-thioformacetal backbones (see, e.g., Jones et al., 1993, J. Org. Chem. 58:2983) and sulfamate backbones (see, e.g., U.S. Pat. No. 5,470,967). All of the preceding references are herein incorporated by reference.

"Peptide Nucleic Acid" or "PNA" refers to poly- or oligonucleotide mimics in which the nucleobases are connected by amino linkages (uncharged polyamide backbone) such as described in any one or more of U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,451,968, 6,441,130, 6,414,112 and 6,403,763; all of which are incorporated herein by reference. The term "peptide nucleic acid" or "PNA" shall also apply to any oligomer or polymer comprising two or more subunits of those polynucleotide mimics described in the following publications: Lagriffoul et al., 1994, Bioorganic & Medicinal Chemistry Letters, 4: 1081-1082; Petersen et al., 1996, Bioorganic & Medicinal Chemistry Letters, 6: 793-796; Diderichsen et al., 1996, Tett. Lett. 37: 475-478; Fujii et al., 1997, Bioorg. Med. Chem. Lett. 7: 637-627; Jordan et al., 1997, Bioorg. Med. Chem. Lett. 7: 687-690; Krotz et al., 1995, Tett. Lett. 36: 6941-6944; Lagriffoul et al., 1994, Bioorg. Med. Chem. Lett. 4: 1081-1082; Diederichsen, U., 1997, Bioorganic & Medicinal Chemistry 25 Letters, 7: 1743-1746; Lowe et al., 1997, J. Chem. Soc. Perkin Trans. 1, 1: 539-546; Lowe et al., 1997, J. Chem. Soc. Perkin Trans. 11: 547-554; Lowe et al., 1997, I. Chem. Soc. Perkin Trans. 1 1:5 55-560; Howarth et al., 1997, I. Org. Chem. 62: 5441-5450; Altmann, K-H et al., 1997, Bioorganic & Medicinal Chemistry Letters, 7: 1119-1122; Diederichsen, U., 1998, Bioorganic & Med. Chem. Lett., 8:165-168; Diederichsen et al., 1998, Angew. Chem. mt. Ed., 37: 302-305; Cantin et al., 1997, Tett. Lett., 38: 4211-4214; Ciapetti et al., 1997, Tetrahedron, 53: 1167-1176; Lagriffoule et al., 1997, Chem. Eur. 1.'3: 912-919; Kumar et al., 2001, Organic Letters 3(9): 1269-1272; and the Peptide-Based Nucleic Acid Mimics (PE-NAMs) of Shah et al. as disclosed in WO 96/04000. All of which are incorporated herein by reference.

Some examples of PNAs are those in which the nucleobases are attached to an N-(2-aminoethyl)-glycine backbone, i.e., a peptide-like, amide-linked unit (see, e.g., U.S. Pat. No. 5,719,262; Buchardt et al., 1992, WO 92/20702; Nielsen et al., 1991, Science 254:1497-1500). A partial structure of N-(2-aminoethyl)-glycine PNA, a PNA suitable for use in the methods and compositions described herein is illustrated in structure (I), below:

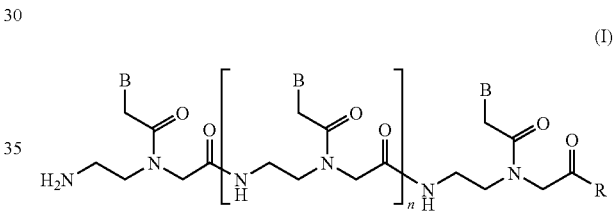

(I)

wherein:
n is an integer that defines the length of the N-(2-aminoethyl)-glycine PNA;
each B is independently a nucleobase; and
R is —OR' or —NR'R', where each R' is independently hydrogen or $(C_1-C_6)$ alkyl, preferably hydrogen.

"Chimeric Oligo" refers to a nucleobase polymer or oligomer comprising a plurality of different polynucleotides, polynucleotide analogs and polynucleotide mimics. For example a chimeric oligo may comprise a sequence of DNA linked to a sequence of RNA. Other examples of chimeric oligos include a sequence of DNA linked to a sequence of PNA, and a sequence of RNA linked to a sequence of PNA.

"Detectable Label" refers to a moiety that, when attached to a moiety described herein, e.g., a sequencing primer, a nucleoside triphosphate, or a terminator, renders such a moiety detectable using known detection methods, e.g., spectroscopic, photochemical, electrochemiluminescent, and electrophoretic methods. Exemplary labels include, but are not limited to, fluorophores and radioisotopes. Such labels allow direct detection of labeled compounds by a suitable detector, e.g., a fluorometer.

"Watson/Crick Base-Pairing" refers to a pattern of specific pairs of nucleobases and analogs that bind together through sequence-specific hydrogen-bonds, e.g. A pairs with T and U, and G pairs with C.

"Nucleoside" refers to a compound comprising a purine, deazapurine, or pyrimidine nucleobase, e.g., adenine, guanine, cytosine, uracil, thymine, 7-deazaadenine, 7-deazaguanosine, and the like, that is linked to a pentose at the 1'-position. When the nucleoside nucleobase is purine or 7-deazapurine, the pentose is attached to the nucleobase at the 9-position of the purine or deazapurine, and when the nucleobase is pyrimidine, the pentose is attached to the nucleobase at the 1-position of the pyrimidine, (see e.g., Kornberg and Baker, DNA Replication, 2nd Ed. (Freeman, San Francisco, 1992)). The term "nucleotide" as used herein refers to a phosphate ester of a nucleoside, e.g., a triphosphate ester, wherein the most common site of esterification is the hydroxyl group attached to the C-5 position of the pentose. The term "nucleoside/tide" as used herein refers to a set of compounds including both nucleosides and nucleotides.

"Annealing" or "Hybridization" refers to the base-pairing interactions of one nucleobase polymer with another that results in the formation of a double-stranded structure, a triplex structure or a quaternary structure. Annealing or hybridization can occur via Watson-Crick base-pairing interactions, but may be mediated by other hydrogen-bonding interactions, such as Hoogsteen base pairing.

"Terminator" or "terminating nucleotide" refers to an enzymatically-incorporable nucleotide or nucleotide analog in which the sugar moiety does not support incorporation of subsequent nucleotides or nucleotide analogs. Typical terminators are those in which the nucleobase is a purine, a 7-deaza-purine, a pyrimidine, a normal nucleobase or a common analog thereof and the sugar moiety is a pentose that includes a 3'-substituent that blocks further synthesis, such as a dideoxynucleotide (i.e., ddNTP). Substituents that block fuirther synthesis include, but are not limited to, amino, deoxy, halogen, alkoxy and aryloxy groups. Exemplary terminators include, but are not limited to, those in which the sugar-phosphate ester moiety is 3'-($C_1$-$C_6$)alkylribose-5'-triphosphate, 2'-deoxy-3'-($C_1$-$C_6$)alkylribose-5'-triphosphate, 2'-deoxy-3'-($C_1$-$C_6$)alkoxyribose-5-triphosphate, 2'-deoxy-3'-($C_5$-$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate.

"Deoxynucleotides" or "dNTPs" refer to deoxynucleoside triphosphate precursors, i.e., dATP, dTTP, dGTP, and dCTP, and dUTP.

5.2 Exemplary Embodiments

The compositions and methods described herein find use in nucleic acid sequencing reactions that involve an extension/termination reaction using an oligonucleotide primer. The oligonucleotide primer can be a synthetic oligonucleotide or a restriction fragment isolated from a template polynucleotide and/or a sequence of interest that hybridizes to a region of the template adjacent to, within the 3' end of the sequence of interest, or a region that comprises the template polynucleotide and the 3'end of the sequence of interest. Primed synthesis is carried out in the presence of a terminator so that the growing chains are randomly terminated by the incorporation of the terminator. Although reaction conditions can be adjusted such that the majority of the primer extension products generated are in specified size range, for example, 50 to 500 base pairs, some of the extension products will be longer than 500 base pairs and can include sequences that are not part of the sequence of interest. Primer extension beyond a predetermined base pair can be prevented or reduced by inclusion of a blocking probe in the sequencing reaction. To avoid detecting base pairs from a sequence that is not part of the sequence of interest, the blocking probe can be designed to hybridize to a sequence adjacent to the 5'-terminus of the sequence of interest.

By "sequence of interest" or "target sequence" herein is meant a nucleobase sequence to be determined using a sequencing technique based on the enzymatic method of Sanger et al. (Sanger et al., 1977, Proc. Natl. Acad. Sci., 74: 5463-5467). It is to be understood that the nature of the sequence of interest is not a limitation of the disclosed compositions and methods. For example, in some embodiments, the sequence of interest occurs in nature and can be DNA (e.g., cDNA, genomic DNA, extrachromosomal DNA) or RNA (e.g., mRNA, rRNA or genomic RNA). In other embodiments, the sequence of interest can be a synthetic or artificial nucleobase sequence comprising nucleotide analogs, mimics, or chimeric oligonucleotides as described above. Generally, each sequence of interest comprises an nucleobase sequence that is not present in the priming sequence, blocking sequence, vector, or other sequences, such as PCR amplification primers, used in the methods and compositions described herein.

In some embodiments, the sequence of interest can be an amplicon generated by any suitable amplification technique including, but not limited to PCR, OLA, LCR. RCA, and RT-PCR (see, e.g., U.S. Pat. Nos. 4,683,195, 4,683,202, 4,800,159, 4,965,188, 5,075,216, 5,130,238, 5,176,995, 5,185,243, 5,354,668, 5,386,022, 5,427,930, 5,455,166, 5,516,663, 5,656,493, 5,679,524, 5,686,272, 5,869,252, 6,025,139 6,040,166; 6,197,563, 6,297,016, 6,514,736, EP-A-0200362, EP-A-0201184, and EP-A-320308). The particular method used is not a critical part of the present disclosure. Amplicons suitable for use in the methods and compositions described herein can be obtained from cells, cell lysates, and tissue lysates. Additionally, other sequences, such as a priming sequence for a sequencing primer and/or a blocking sequence for a blocking probe can be added during the amplification process.

In some embodiments, the priming sequence and/or the blocking sequence are added to the sequence of interest during an amplification reaction. For example, an amplification reaction that couples an exponential phase with a linear phase can be used to generate a sequence of interest flanked at the 3' end by the priming sequence, and at the 5' end by the blocking sequence. In exponential sequence amplification, the product of each amplification cycle is an amplicon that is a suitable template for subsequent amplification cycles. Therefore, as known in the art, exponential amplification generally utilizes at least two or paired exponential primers. For example, the exponential amplification of a target sequence by PCR generally utilizes a pair of "forward" and "reverse" primers. Therefore, the skilled artisan is aware that the suitability of a primer for exponential amplification depends, in part, on the presence of a second suitable primer. The forward and reverse primers hybridize to a sequence of interest in opposite orientations to produce complementary DNA strands to form double-stranded amplicons that serve as templates for further rounds of amplification. By "linear primer" and "linear amplification primer" herein are meant a primer suitable to linearly amplify a polynucleotide sequence. In linear sequence amplification, the product of each amplification cycle is not suitable for subsequent amplification cycles. For example, the linear amplification of a sequence generally produces a single-stranded amplicon that does not hybridize to the linear primer and, therefore, is not a suitable template for subsequent amplification cycles. As a result, in some embodiments, linear amplicons accumulate at a rate proportional to the number of templates.

Methods employing exponential and linear amplification reactions to amplify polynucleotides are disclosed, for example, in U.S. Patent Application No. 60/584,665 filed Jun. 30, 2004. Methods of exponentially amplifying polynucleotide sequences of interest via the polymerase chain reaction (PCR) are described in, e.g., U.S. Pat. Nos. 4,683,195, 4,683,202, 4,800,159, 4,965,188, 5,075,216, 5,176,995, 5,386,022, 5,333,675, 5,656,493, 6,040,166, 6,197,563, 6,514,736, and EP-A-0200362 and EP-A-0201184. Methods of exponentially amplifying polynucleotide sequences via the ligase chain reaction are described in, e.g., U.S. Pat. Nos. 5,427,930, 5,516,663, 5,686,272, 5,869,252 and EP-A-320308. Methods of linearly amplifying polynucleotides sequences of interest via polymerization reactions are described in, e.g., U.S. Pat. Nos. 5,066,584, 5,891,625 and WO 93/25706. Methods of linearly amplifying polynucleotide sequences of interest via ligation reactions are described in, e.g., U.S. Pat. Nos. 5,185,243 and 5,679,524. All of these various methods can be utilized in various combinations to amplify polynucleotides via the log-linear methods described herein.

Generally, each amplification primer should be sufficiently long to prime template-directed synthesis under the conditions of the disclosed methods. The exact lengths of the primers may depend on many factors, including but not limited to, the desired hybridization temperature between the primers and template polynucleotide(s), the complexity of the template polynucleotide sequence to be amplified, the salt concentration, ionic strength, pH and other buffer conditions, and the sequences of the primers and template polynucleotides. The ability to select lengths and sequences of primers suitable for particular applications is within the capabilities of ordinarily skilled artisans (see, e.g., Sambrook et al. *Molecular Cloning: A Laboratory Manual* 9.50-9.51, 11.46, 11.50 (2d. ed., Cold Spring Harbor Laboratory Press); Sambrook et al., *Molecular Cloning: A Laboratory Manual* 10.1-10.10 (3d. ed. Cold Spring Harbor Laboratory Press)).

The concentration of an amplification primer may vary widely and in various embodiments, may be limiting or non-limiting. "Limiting concentration" refers to a concentration of a reagent, such as, an amplification primer, that determines the rate at which a reaction may proceed and/or the time point at which a reaction terminates. Conversely, "non-limiting concentration" refers to a concentration of a reagent at the point a reaction initiates that may not determine the rate at which the reaction may proceed and/or the time point at which the reaction terminates. A skilled artisan will appreciate, however, that in some embodiments a reagent at a non-limiting concentration may become limiting as the reagent is consumed during the course of the reaction. In some embodiments, a limiting concentration of an amplification primer terminates the amplification reaction before it reaches a plateau. In some embodiments, the concentration of an amplification primer can be adjusted so that a selected number of amplicons are generated. Determining the appropriate concentration of one or more amplification primers is within the abilities of the skilled artisan. Examples of factors to be considered include, but are not limited to, the quantity of the template polynucleotide, the relative amount of the template polynucleotide sequence to be amplified, the sensitivity of the detection system, and the degree of accuracy desired.

Figure 1:
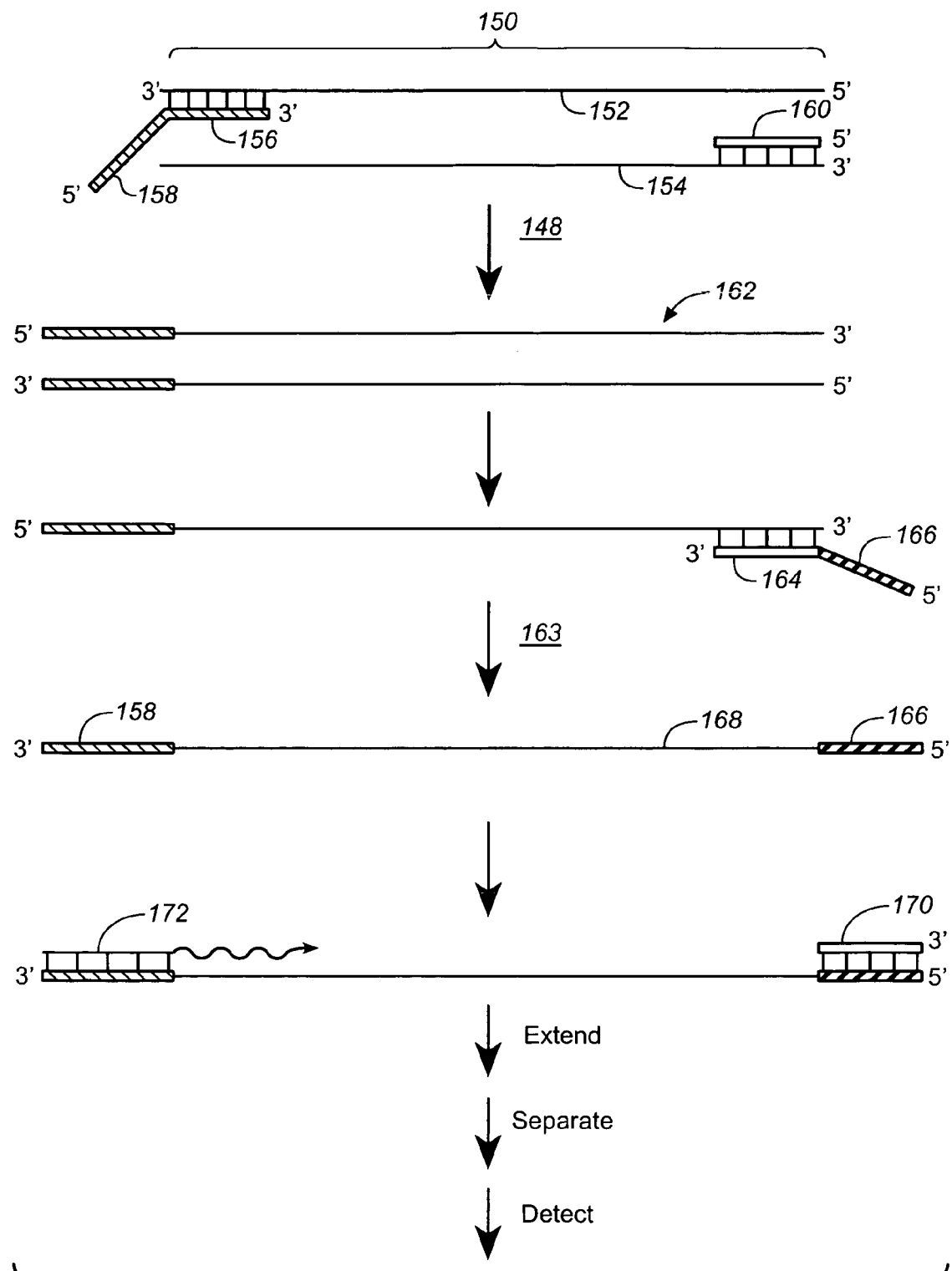
FIG. 1 illustrates an embodiment of a method for directly sequencing an amplification product obtained by a log-linear amplification technique.

Thus, in some embodiments, an exponential PCR amplification can be linked to a linear amplification to create a log-linear amplification reaction. The resulting product can be sequenced using one of the sequencing methods described below. One such embodiment is illustrated in FIG. 1. In FIG. 1, an exponential PCR amplification 148 is carried out in the presence of an amplicon comprising the sequence of interest 150, forward amplification primer 156, and reverse amplification primer 160. The forward primer comprises a 5' tail 158 that comprises a priming sequence. As discussed below, the priming sequence can be a specific sequence or a universal sequence. Product 162 of the exponential amplification is used as the template in a linear amplification 163 in the presence of amplification primer 164. Primer 164 comprises a 5' tail 166. Tail 166 comprises a blocking sequence, which can be a specific sequence or a universal sequence (discussed in detail below). The single-stranded product 168 comprises both a priming sequence 158 and a blocking sequence 166. Sequencing primer 172 and blocking probe 170 can hybridize as shown for use in a sequencing reaction as described herein. The amplification can be monitored in real-time by any of a variety of methods known to those of skill in the art.

In some embodiments, the sequence of interest is present on a polynucleotide that can be used as a template in the sequencing reactions described herein. The polynucleotide may be provided from any source. For example, the polynucleotide may exist as part of a nucleobase polymer or oligomer, polynucleotide or oligonucleotide, polynucleotide or oligonucleotide analog, polynucleotide or oligonucleotide mimic, or chimeric oligo. The sample containing the polynucleotide may be provided from nature or it may be synthesized or supplied from a manufacturing process.

In some embodiments, preparation of the polynucleotide template for sequencing may not be required. In other embodiments, conventional sample preparation techniques, such as chromatography, precipitation, electrophoresis, etc., can be used to prepare the polynucleotide as a template for the sequencing reactions described herein. The polynucleotide can be obtained from any source and amplified. For example, the polynucleotide can be produced from an amplification process, contained in a cell or organism or otherwise be extracted from a cell or organism. Examples of amplification processes that can be the source for the polynucleotide include, but are not limited to, Polymerase Chain Reaction (PCR), Ligase Chain Reaction (LCR), Strand Displacement Amplification (SDA; see, e.g., Walker et al., 1989, PNAS 89:392-396; Walker et al., 1992, Nucl. Acids Res. 20(7): 1691-1696; Nadeau et al., 1999, Anal. Biochem. 276(2):177-187; and U.S. Pat. Nos. 5,270,184, 5,422,252, 5,455,166 and 5,470,723), Transcription-Mediated Amplification (TMA), Q-beta replicase amplification (Q-beta), Rolling Circle Amplification (RCA), Lizardi, 1998, Nat. Genetics 19(3): 225-232 and U.S. Pat. No. 5,854,033), or Asynchronous PCR (see, e.g., WO 01/94638).

The polynucleotide can be single or double-stranded, or a combination thereof, linear or circular, a chromosome or a gene or a portion or fragment thereof. In other embodiments, the polynucleotide can be a restriction fragment from, for example, a plasmid, a library (e.g., YAC, BAC, PAC, cDNA), chromosomal DNA, extrachromosomal DNA (e.g., mitochondrial DNA), RNA (e.g., mRNA, rRNA, or vRNA), or cDNA. Polynucleotides that do not exist in a single-stranded state can be rendered single-stranded prior to initiation of the sequencing reaction using methods known to those of skill in the art, such as, denaturation by heat or alkali, digestion with an exonuclease, or denaturation by heat during cycle sequencing. See, e.g., Sambrook and Russell, 2001, *Molecular Cloning: A Laboratory Manual*, 3$^{rd}$ Edition, Chapter 12, Cold Spring Harbor Laboratory Press.

Figure 2:
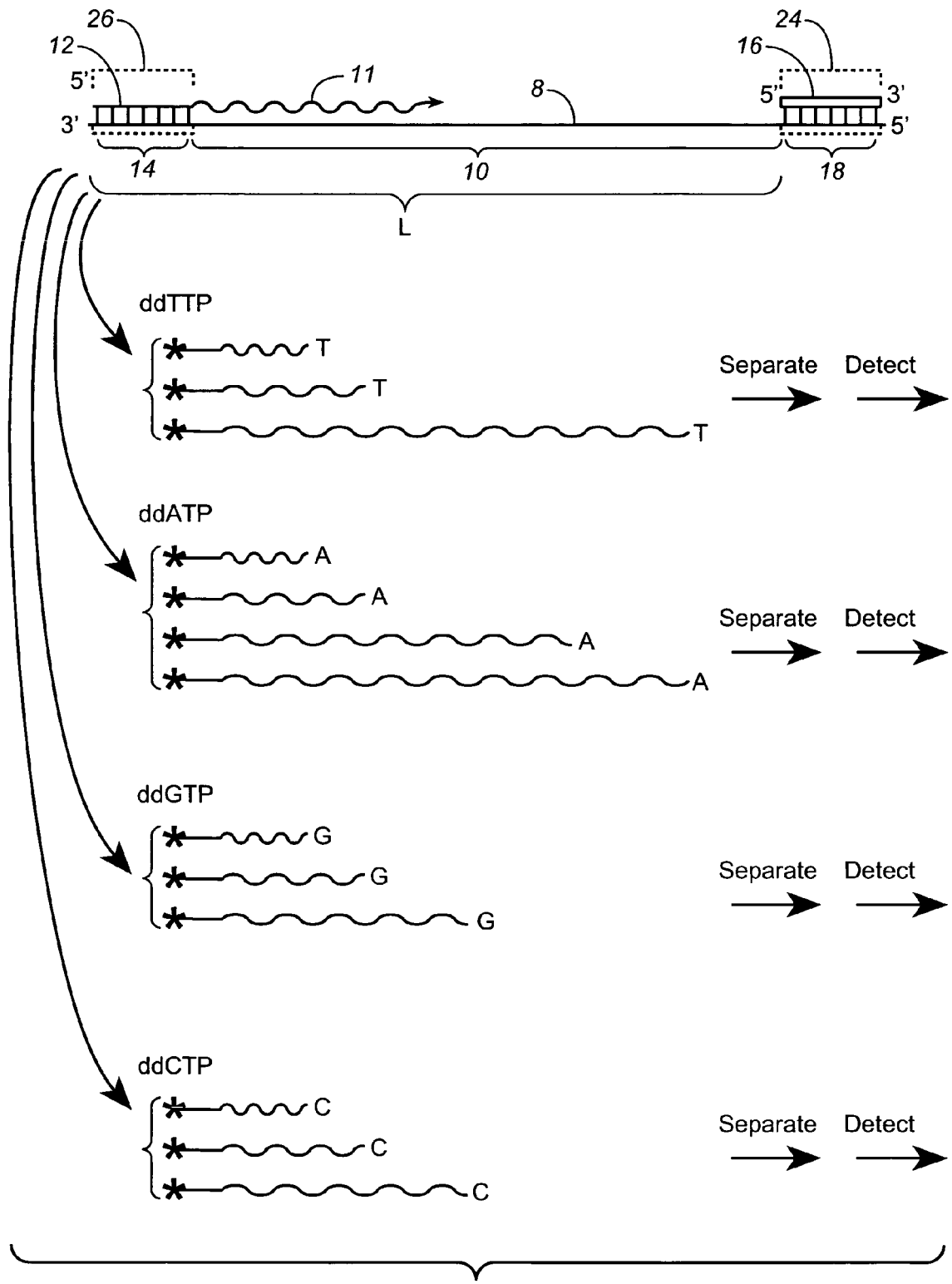
FIG. 2 illustrates an embodiment of a sequencing reaction utilizing labeled sequencing primers.

In addition to the sequence of interest, the polynucleotide template can comprise additional nucleobase sequences. FIG. 2 illustrates an exemplary embodiment in which polynucleotide template 8 comprises sequence of interest 10, priming sequence 14, and blocking sequence 18. Although the embodiment illustrated in FIG. 2 depicts the polynucleotide template as comprising a sequence of interest, priming sequence and blocking sequence, other embodiments can be used in the methods and compositions described herein. For example, in some embodiments, the polynucleotide template can comprise the sequence of interest, the blocking probe, the priming sequence and a vector sequence. In other embodiments, the polynucleotide template can comprise the sequence of interest and the blocking sequence. In yet other embodiments, the polynucleotide template can comprise the sequence of interest and the priming sequence. Additionally, the polynucleotide template can include other sequences, selected by the user, depending, in part, on whether the sequence of interest is an amplicon or cloned insert. For example, in some embodiments, the template can comprise restriction endonuclease sites between which the sequence of interest can be inserted. Thus, various sequence combinations can be present in the polynucleotide template used in the methods and compositions described herein.

In the embodiment illustrated in FIG. 2, the polynucleotide template comprises a priming sequence 14, sequence of interest 10 and blocking sequence 18. Hybridization complex 26 provides a "priming site" for the enzymatic addition of dNTPs to primer 12 such that primer extension products are generated. The extent of complementarity between primer 12 and priming sequence 14 will depend, in part, on the type of polymerase used in the sequencing reactions. For example, if a polymerase lacking exonuclease activity is used in the sequencing reactions, at a minimum, the terminal base at the 3'-end of primer 12 should be completely complementary to the corresponding base in priming sequence 14. If the polymerase used in the sequencing reaction has exonuclease activity, primer 12 can comprise a sequence that produces one or more mismatches within the primer/priming sequence complex. The mismatches can be located internally, as well as at the 5'- and 3'-ends. Thus, primers comprising no mismatches, one mismatch, or two or more mismatches can be used, provided that the primer and priming sequence form a complex that provides a priming site for the enzymatic addition of dNTPS.

In some embodiments, primer 12 can be completely complementary to priming sequence 14. In other embodiments, the nucleobase sequence of primer 12 can be substantially complementary to priming sequence 14. By "substantially complementary" herein is meant that the primer comprises a sequence that produces a single mismatch within the primer/priming sequence complex. In yet other embodiments, primer 12 comprises a sequence that produces two or more mismatches within the primer/priming sequence complex.

The priming sequence can be a universal sequence or can comprise a sequence that is complementary to a specific primer. Generally, priming sequences lack significant homology with the blocking sequence, blocking probe, other sequences present in the template polynucleotide, and/or with regions of the sequence of interest that do not include the 3'-end of the sequence of interest. Methods for designing priming sequences suitable for hybridizing to a sequencing primer are well known in the art (see, e.g., Sambrook and Russell, 2001, *Molecular Cloning: A Laboratory Manual*, 3$^{rd}$ Edition, Chapter 8, Cold Spring Harbor Laboratory Press). For example, the polynucleotide template and/or the 3' end of the sequence of interest can be analyzed using available computer programs for potential priming sequences that are free of homopolymeric tracts, have no obvious tendency to form secondary structures, are not self-complementary, and have no significant homology with the remainder of the sequence of interest or the blocking sequence, the blocking probe, or other sequences present in the template polynucleotide (see, e.g., BLAST, Altschul et al., 1990, J. Mol. Bio. 215: 403-410). In other embodiments, the priming sequence can be a "universal sequence" present in commercially available vectors used for Sanger-type sequencing reactions. See, e.g., Sambrook and Russell, 2001, *Molecular Cloning: A Laboratory Manual*, 3$^{rd}$ Edition, Chapter 12, Cold Spring Harbor Laboratory Press.

The priming sequence should be sufficiently long such that a stable complex with the sequencing primer is formed. The exact length of the priming sequence can depend on a number of factors, including, but not limited to, the desired hybridization temperature between the primer and the priming sequence, salt concentration, ionic strength, pH and other buffer conditions, and the sequence of the primer. The ability to select lengths and sequences of priming sequences suitable for a particular application is within the capabilities of a person skilled in the art (see, e.g., Sambrook and Russell, 2001, *Molecular Cloning: A Laboratory Manual*, 3$^{rd}$ Edition, Chapters 8 and 12, Cold Spring Harbor Laboratory Press). In some embodiments, priming sequences can be between 1 to 50 nucleobases in length. For example, priming sequences that range between 1 to 5 nucleobase in length, 6 to 10 nucleobases in length, 10 to 15 nucleobases in lengthn, 15 to 30 nucleobases in length, and from 40 to 50 nucieobases in length can be used in the methods and compositions described herein.

The priming sequence should be positioned such that the resulting primer extension products comprise all or a portion of the sequence of interest. In some embodiments, the priming sequence can be located adjacent to the 3' end of the sequence of interest. In other embodiments, the priming sequence can comprise the 3' end of the sequence of interest. In other embodiments, the priming sequence comprises a portion of the template polynucleotide and the 3'end of the sequence of interest. See, e.g., U.S. Pat. No. 6,258,568, and Sanger, 1981, Science, 214: 1205-1210.

As discussed above, the priming sequence is designed to form a stable complex with a sequencing primer. The resulting stable complex serves as an initiation site for primer extension. By "primer extension" herein is meant the polymerase catalyzed esterification of a dNTP with the 3'-terminal nucleotide of the primer. Thus, the sequencing primers used in the methods and compositions described herein typically have a free 3'-hydroxyl group to allow chain extension by a polymerase. The primers can be completely or substantially complementary to the priming sequence. Finally, the primers should be sufficiently long to hybridize to form a stable duplex with the priming sequence. In some embodiments, the primer can be chosen to hybridize at least one base in from the 3' end of the template polynucleotide to eliminate blunt-ended DNA polymerase activity (see U.S. Pat. No. 6,258, 568). In some embodiments, "universal primers" are used. Universal primers having these characteristics are available from a large number of commercial companies, and are typically 15-30 nucleotides in length. Suitable universal primers for use in the methods and compositions described herein include, but are not limited to, λgt10 forward and reverse primers, λgt11 forward and reverse primers, pUC/N13 forward and reverse primers, SP6 universal primer, T7 universal primer, and T3 promoter primer.

In other embodiments, primers can be generated using fragments resulting from restriction endonuclease digestion of the sequence of interest or the polynucleotide comprising the sequence of interest (Sanger, 1981, Science, 214: 1205-1210). In other embodiments, primers can be designed and synthesized to be complementary to a priming sequence using methods known in the art (see e.g., above discussion for designing priming sequences, and Sambrook and Russell, 2001, *Molecular Cloning: A Laboratory Manual*, 3$^{rd}$ Edition, Chapter 8, Cold Spring Harbor Laboratory Press). Designed primers can be between 10 to 100 nucleobases in length. In other embodiments, designed primers can be between 15 to 50 nucleobases in length. In yet other embodiments, designed primers can be between 15 to 30 nucleobases in length.

The chemical composition of the sequencing primer is not critical to the success of the compositions and methods described herein. Virtually any nucleobase oligomer that is capable of hybridizing to the priming sequence in a sequence-specific manner and that is capable of initiating the primer extension reaction may be used in the compositions and methods described herein. Generally, oligonucleotide sequencing primers are used in the compositions and methods described herein.

In the embodiment illustrated in FIG. 2, in addition to priming sequence 14 and sequence of interest 10, the polynucleotide template comprises a blocking sequence 18. The extent of complementarity between blocking sequence 18 and blocking probe 16 can vary, provided that blocking sequence 18 and blocking probe 16 form a stable complex 24 that typically is not displaced during the primer extension reaction. Thus, in some embodiments, blocking sequence 18 can be completely complementary to blocking probe 16. In other embodiments, the nucleobase sequence of blocking sequence 18 can be substantially complementary to blocking probe 16. In other embodiments, blocking sequences comprising two or more mismatches can be used.

The blocking sequence can be a universal sequence or can comprise a sequence that is complementary to a specific blocking probe. The blocking sequences described herein typically lack significant homology with the priming sequence, sequencing primer, other sequences present in the template polynucleotide, or in the sequence of interest, are free of homopolymeric tracts, have no obvious tendency to form secondary structures, and are not self-complementary. Methods for designing sequences suitable for hybridizing to a blocking probe are well known in the art (see, e.g., Sambrook and Russell, 2001, *Molecular Cloning: A Laboratory Manual*, 3$^{rd}$ Edition, Chapter 8, Cold Spring Harbor Laboratory Press). In some embodiments, the polynucleotide comprising the sequence of interest can be analyzed using available computer programs for potential blocking sequences that are free of homopolymeric tracts, have no obvious tendency to form secondary structures, are not self-complementary, have no significant homology with the sequence of interest or the priming sequence and the desired T$_m$ (see, e.g., BLAST, Altschul et al., 1990, J. Mol. Bio. 215: 403-410).

In other embodiments, the blocking sequence can be a "universal sequence" present in commercially available vectors used for Sanger-type sequencing reactions. See, e.g., Sambrook and Russell, 2001, *Molecular Cloning: A Laboratory Manual*, 3$^{rd}$ Edition, Chapter 12, Cold Spring Harbor Laboratory Press.

The blocking sequence should be sufficiently long such that a stable complex with the blocking probe is formed. As discussed above, the exact length of the blocking sequence can depend on a number of factors, including, but not limited to, the desired hybridization temperature between the blocking probe and the blocking sequence, salt concentration, ionic strength, pH and other buffer conditions, and the sequence of the blocking probe. Generally, blocking sequences are between 10 to 100 nucleobases in length. In some embodiments, the blocking sequence can be between 10 to 20 nucleobases in length. In other embodiments, the blocking sequence can be between 10 to 30 nucleobases in length. In yet other embodiments, the blocking sequence can be between 15 to 30 nucleobases in length.

In some embodiments, the blocking sequence comprises PNA. In these embodiments, the blocking sequence can be between 15 to 20 nucleobases in length.

As illustrated in FIG. 2, blocking sequence 18 is located at the 5' end of the sequence of interest 10. The location of blocking sequence 18 with respect to the 5' end of the sequence of interest can be selected by the user, depending in part, on the last base to be sequenced, the number of incorporation events that can occur beyond the last base to be sequenced as a consequence of "end-breathing", and the extent to which the electrophoretic peak corresponding to the last base is shifted due to the presence of unlabeled products present in the sequencing reaction. If "N" corresponds to the last base for which sequence information is desired, then the blocking sequence can be located "X" number of bases from N. "X" can equal 0, 1, 2, 3, 4, 5, 6, 7, 8, 9, 10, 11, 12, 13, 14, 15, 16, 17, 18, 19 and 20 bases. As will be appreciated by the skilled artisan, other values for X are also possible, provided that the number of incorporation events that occur after N are minimal, and little or no peak shifting occurs. The blocking sequence is typically located such that the number of incorporation events after N is zero. In other embodiments, the blocking sequence can be located such that the number of incorporation events beyond N is reduced. For example, the blocking sequence can be located such that only one incorporation event after N occurs. In another specific example, the blocking sequence can be located such that two incorporation events after N occur.

Typically, the user can select the base corresponding to N. For example, if sequence information for all of the bases comprising the sequence of interest is desired, N can correspond to the base located at the 5' terminus of the sequence of interest. As another example, if sequence information for a particular region of the sequence of interest is desired, N can correspond to a base located within the sequence of interest, such as a base located adjacent to the 5'-terminus, or within the sequence of interest. Thus, the location of the blocking sequence can be positioned such that the resulting population of primer extension products lies within a selected size range and comprises all or a portion of the sequence of interest.

The chemical composition of the blocking sequence is not critical to the success of the disclosed compositions and methods. Virtually any nucleobase oligomer that is capable of hybridizing to a blocking probe in a sequence-specific manner may be used to block or reduce the generation of primer extension products beyond the sequence of interest. For example, the blocking sequence can include, but is not limited to, oligonucleotides, oligonucleotide analogs, oligonucleotide mimics such as PNAs and chimeric oligonucleotides, as defined above. In some embodiments, the blocking sequence is an oligonucleotide.

Examples of blocking sequences suitable for use in the methods and compositions described herein are depicted in Table 1.

TABLE 1

| SEQ ID NO. | Type | Sequence* |
|---|---|---|
| 1 | DNA | AATAAACTGCAGAACC |
| 2 | DNA | CTGCAGAACCAATGCAG |

TABLE 1-continued

| SEQ ID NO. | Type | Sequence* |
|---|---|---|
| 3 | DNA | GCAGAACCAATGCAGG |
| 4 | DNA | AGAACCAATGCAGGTC |
| 5 | DNA | AAACTGCAGAACCAAT |

*Sequences are presented in the 5' → 3' direction

In the exemplary embodiment illustrated in FIG. 2, blocking probe 16 is capable of forming hybridization complex 24 with blocking sequence 18. It is not essential to the methods described herein that the blocking probe be designed to bind only to "unique" sequence(s). The sequence of the blocking probe can comprise any combination of bases capable of binding to sequences comprising the blocking sequence, as well as other sequences present in the polynucleotide template, as long as hybridization of the blocking probe to the blocking sequence results in the formation of stable complex, beyond which, the generation of primer extension products is reduced or prevented.

In some embodiments, blocking probes can be designed to hybridize to a blocking sequence in a sequence specific manner. The blocking probes described herein typically have no significant homology with the priming sequence, sequencing primers, other sequences present in the template polynucleotide, or the sequence of interest. In some embodiments, the blocking probe can bind a "universal sequence" present in commercially available vectors used for Sanger-type sequencing reactions. See, e.g., Sambrook and Russell, 2001, *Molecular Cloning: A Laboratory Manual*, 3$^{rd}$ Edition, Chapter 12, Cold Spring Harbor Laboratory Press. Available computer programs can be used to screen commercially available vectors for sequences that do not form hybridization complexes with commercially available primers used in sequencing or PCR reactions, but that can form a hybridization complex with a blocking probe used in the methods and compositions described herein.

Blocking probes useful in the methods and compositions described herein typically lack homopolymeric tracts, have little tendency to form secondary structures, generally are not self-complementary, and lack significant homology with sequences present in the polynucleotide template. The degree of homology between the blocking probe, the blocking sequence and other sequences comprising the polynucleotide template can be determined empirically. Methods for designing nucleobase oligomers that can be used as a blocking probe are well known in the art (see, e.g., Sambrook and Russell, 2001, *Molecular Cloning: A Laboratory Manual*, 3$^{rd}$ Edition, Chapter 8, Cold Spring Harbor Laboratory Press). For example, in some embodiments, available computer programs can be used to analyze the polynucleotide template for potential blocking sequences to which complementary blocking probes can be made (see, e.g., BLAST, Altschul et al., 1990, J. Mol. Bio. 215: 403-410), Osborne, CABIOS, 8: 83 (1991); Montpetit et al., J. Virol. Methods, 36: 119-128 (1992). In other embodiments, available computer programs can be used to screen nucleic acid sequences deposited in public databases for potential blocking probes. In other embodiments, artifical nucleobase oligomers can be synthesized comprising a random sequence of nucleobases. Random nucleobase sequences can be generated using a Random Number Program. A number of Random Number Programs can be used, see e.g., Random Number Generator Pro (Sego-bit Software), Really Random Numbers (Sunny Beach Technology, Inc.), ZRandom for Excel 1.2 (Regnow).

Typically, the blocking probe is not a template for primer extension, e.g., the blocking probe should be non-extendible. However, in some embodiments, the blocking probe can be extendible, provided that the extension products so generated do not interfere with the sequencing reaction.

The blocking probe should be sufficiently long such that a stable complex with the blocking sequence is formed. The exact length of the blocking probe can depend on a number of factors, including, but not limited to, the desired hybridization temperature between the blocking probe and the blocking sequence, salt concentration, ionic strength, pH and other buffer conditions, and the sequence of the blocking probe. The ability to select lengths and sequences of blocking probes suitable for a particular application is within the capabilities of a person skilled in the art (see, e.g., Sambrook and Russell, 2001, *Molecular Cloning: A Laboratory Manual*, 3$^{rd}$ Edition, Chapters 8 and 12, Cold Spring Harbor Laboratory Press). Generally, blocking probes will have a length between 10 to 100 nucleobases. In some embodiments, blocking probes can be between 15 to 30 nucleobases in length. In other embodiments, the blocking probes can be between 12 to 20 nucleobases in length.

The extent of complementarity between blocking probe 16 and blocking sequence 18 will depend, in part, on the type of sequencing reaction used. For example, if thermal cycle nucleic acid sequencing is used, then blocking probes that are complementary or substantially complementary to the blocking sequence typically are used. If low temperature isothermal nucleic acid sequencing is used, then blocking probes with no mismatches, one mismatch, or two or more mismatches can be used. Irrespective of the type of sequencing reaction used, blocking probes comprising no mismatches, one mismatch, or two or more mismatches can be used in the methods and compositions described herein, provided that the blocking probe is capable of binding the blocking sequence before the polymerase used in the sequencing reaction begins to generate primer extension products.

The chemical composition of the blocking probe is not critical to the success of the disclosed compositions and methods. Virtually any nucleobase oligomer that is capable of hybridizing to a blocking sequence in a sequence-specific manner may be used in the compositions and methods described herein. Thus, blocking probes useful in the compositions and methods described herein include, but are not limited to, oligonucleotides, oligonucleotide analogs, oligonucleotide mimics such as PNAs and chimeric oligonucleotides, as defined above. In some embodiments, the blocking probes can be resistant to degradation by nucleases (e.g., exonucleases and/or endonucleases). Nuclease-resistant probes include, by way of example and not limitation, oligonucleotide mimic probes, such as PNA probes. In some embodiments, the blocking probe can be rendered non-extendable by a sequencing polymerase by blocking the 3' end by including, for example, sugar modifications such as a 3'-phosphate, a 3'-acetyl, a 2'-3'-dideoxy, a 3'-amino, and a 2'-3' dehydro, or by adding at least one non-complementary base to the 3' end.

In some embodiments, the blocking probes comprise PNA. Generally, PNA blocking probes can be 12, 13, 14, 15, 16, 17, 18, 19, and 20 nucleotides in length. However, in some embodiments, PNA blocking probes can be greater than 20 nucleotides in length. PNA blocking probes can be designed to form duplexes or triplexes with the blocking sequence. Examples of PNA probes capable of forming triplexes are described, for example, in U.S. Pat. Nos. 6, 420,115 and 6,432,642, incorporated herein by reference in their entirety.

In other embodiments, the blocking probes comprise oligonucleotides or LNAs. For example, blocking probes comprising oligonucleotides or LNAs can be between 15 to 30 nucleotides in length. In other examples, blocking probes comprising oligonucleotides or LNAs can be between 15 to 100 nucleotides in length. In yet other examples, blocking probes comprising oligonucleotides or LNAs can be greater than 100 nucleotides.

Examples of blocking probes suitable for use in the methods and compositions described herein are depicted in Table 2.

TABLE 2

| Name | Type | Sequence* | |
|---|---|---|---|
| PNA3 | PNA | ggttctgcagtttatt | (SEQ ID NO. 6) |
| PNA12 | PNA | ctgcattggttctgcag | (SEQ ID NO. 7) |
| PNA14 | PNA | cctgcattggttgtgc | (SEQ ID NO. 8) |
| PNA16 | PNA | gacctgcattggttct | (SEQ ID NO. 9) |
| PNA9 | PNA | attggttctgcagttt | (SEQ ID NO. 10) |

*Sequences are depicted int the amino-to carboxy direction. "a" is diaminopurine.

Different combinations of blocking probes can be used in the sequencing reactions described herein. For example, in some embodiments, each reaction mixture can comprise a single blocking probe. In embodiments using four separate reaction mixtures, the blocking probe can be the same in each of the reaction mixtures, some of the blocking probes can be the same and others different, or each reaction mixture, independently of the others, can comprise a different blocking probe. As another specific example, in embodiments using a single reaction mixture, two or more blocking probes can be included in the reaction mixture. The blocking probes can be the same or different. In yet another specific example, in embodiments comprising four separate reaction mixtures, each reaction mixture, independently of the other can comprise one, or two or more blocking probes. The blocking probes can be the same in a given reaction mixture or different. As will be appreciated by a person skilled in the art, each of the four separate reactions, independently of the others, can comprise the same blocking probe or a different blocking probe.

In some embodiments, various compounds can be used analogously to the blocking probes to block primer extension in an enzyme-mediated primer extension sequencing reaction. Non-limiting examples of such compounds comprise antibodies having specificity for a particular nucleic acid sequence and small-molecule synthetic ligands having nucleic acid sequence-recognition properties (see, e.g., White et al., 1998, Nature, 391: 468-471; Kielkopf et al., 1998, Nat. Struct. Biol., 5(2): 104-109; Becker et al., 1979, J. Am. Chem. Soc., 101(13): 3664-6).

Typically, blocking probes can be used in any reaction in which it is desirable to terminate the reaction at a pre-determined location. As a specific example, blocking probes can be incorporated in amplification reactions to generate amplification products that terminate at a pre-determined location, e.g., amplification products that terminate at selected pre-determined locations within the sequence being amplified. Other reactions in which blocking probes can be used, include reactions in which it is desirable to generate reaction products within a given size range. For example, as described more fully below, in some embodiments, one or more blocking probes can be included in a sequencing reaction to generate reaction products within a given size range. Reaction products in which the maximum length is pre-determined using a blocking probe can be used in combination with capillary electrophoresis methods in which the samples can be injected sequentially without the need for intervening wash steps, etc.

FIG. 2 illustrates an exemplary embodiment in which blocking probes are used in a sequencing reaction. As illustrate in FIG. 2, extension of primer 12 continues until a terminator, i.e., ddNTP, is incorporated or hybridization complex 24 is reached. Hybridization complex 24 is formed as a result of sequence specific binding between the blocking probe and the blocking sequence. The location of hybridization complex 24 determines the maximum length of the primer extension products for a given sequencing reaction. The maximum length for a population of primer extension products can be selected by the user, depending in part, on the system used to separate the primer extension products and/or on the size of the sequence of interest. For example, if capillary electrophoresis is used to separate the primer extension products, the length of the longest extension product can be 50, 100, 200, 300, 400, 500, 600, 700, 800, 1000, nucleotides or greater depending on the resolution of the polymer used to separate the extension products. In other embodiments, the maximum size can be selected based on the size of the sequence of interest. For example, if the sequence of interest is 100 nucleotides in length, then the maximum size fragment present in the population of primer extension products would be 100 nucleotides.

To block primer extension beyond the sequence of interest, the blocking probe should bind to the blocking sequence before the polymerase used to generate the primer extension products begins to extend the primer. For example, the $T_m$ of the blocking probe can be designed such that the blocking probe remains bound to the blocking sequence throughout the various temperatures used during a sequencing reaction. In other embodiments, the blocking probe can re-anneal to the polynucleotide template prior to the initiation of the primer extension step. This can be achieved by using a blocking probe designed to have a higher $T_m$ than the $T_m$ of the sequencing primer.

The capability of the blocking probe or the sequencing primer to anneal can be determined by the $T_m$ of the hybrid complex. The greater the $T_m$ value, the more stable the hybrid. $T_m$ is the temperature at which 50% of a nucleobase oligomer and its perfect complement form a double stranded oligomer structure. The $T_m$ for a selected nucleobase oligomer also varies with factors that influence or affect hybridization. For example, such factors include, but are not limited to, factors commonly used to impose or control stringency of hybridization, (i.e., formamide concentration (or other chemical denaturant reagent), salt concentration (i.e., ionic strength), hybridization temperature, detergent concentration, pH and the presence or absence of chaotropes. Optimal stringency for forming a hybrid combination can be found by the well-known technique of fixing several of the aforementioned stringency factors and then determining the effect of varying a single stringency factor. The same stringency factors can be modulated to control the stringency of hybridization of a PNA to a nucleic acid, except that the hybridization of a PNA is fairly independent of ionic strength. Optimal or suitable stringency for an assay can be experimentally determined by examination of each stringency factor until the desired degree of discrimination is achieved.

Alternatively, the $T_m$ values for the primers and blocking probes can be calculated using known methods for predicting melting temperatures. See, e.g., Baldino et al. Methods Enzymology. 168:761-777; Bolton et al., 1962, Proc. Natl. Acad. Sci. USA 48:1390; Bresslauer et al., 1986, Proc. Natl. Acad. Sci. USA 83:8893-8897; Freier et al., 1986, Proc. Natl. Acad. Sci. USA 83:9373-9377; Kierzek et al., Biochemistry 25:7840-7846; Rychlik et al., 1990, Nucleic Acids Res. 18:6409-6412 (erratum, 1991, Nucleic Acids Res. 19:698); Rychlik. *J. NIH Res.* 6:78; Sambrook et al. *Molecular Cloning: A Laboratory Manual* 9.50-9.51, 11.46-11.49 (2d. ed., Cold Spring Harbor Laboratory Press); Sambrook et al., *Molecular Cloning: A Laboratory Manual* 10.1-10.10 (3d. ed. Cold Spring Harbor Laboratory Press)); Suggs et al., 1981, In *Developmental Biology Using Purified Genes* (Brown et al., eds.), pp. 683-693, Academic Press; Wetmur, 1991, Crit. Rev. Biochem. Mol. Biol. 26:227-259.

In some embodiments, the $T_m$ of the blocking probe can be between 1° C. to 20° C. greater than the temperature at which the polymerase used to generate the primer extension products begins to extend the primer. For example, if the polymerase used in the sequencing reactions is active at 96° C., than the $T_m$ of the blocking probe can range between 97° C. to 110° C. In another example of the embodiments described herein, if the polymerase used in the sequencing reactions is active at 80° C., than the $T_m$ of the blocking probe can range between 90° C. to 100° C.

The blocking probes and sequencing primers can be synthesized using routine methods. For example, methods of synthesizing oligonucleotide probes are described in U.S. Pat. No. 4,973,679; Beaucage, 1992, Tetrahedron 48:2223-2311; U.S. Pat. No. 4,415,732; U.S. Pat. No. 4,458,066; U.S. Pat. No. 5,047,524 and U.S. Pat. No. 5,262,530; all of which are incorporated herein by reference. The synthesis may be accomplished using automated synthesizers available commercially, for example the Model 392, 394, 3948 and/or 3900 DNA/RNA synthesizers available from Applied Biosystems, Foster City, Calif. Similarly, methods of synthesizing labeled oligonucleotide probes are also well-known. As a specific example, see WO 01/94638 (especially the disclosure at pages 16-21), the disclosure of which is incorporated herein by reference.

Methods of synthesizing labeled and unlabeled oligonucleotide analog probes are well-known in the art. See, for example, U.S. Pat. No. 6,479,650 and U.S. Pat. No. 6,432,642, both of which are incorporated herein by reference in their entirety.

Methods for the chemical assembly of PNAs are well known (see U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,201,103, 6,350,853, 6,357,163, 6,395,474, 6,414,112, 6,441,130, 6,451,968; all of which are herein incorporated by reference; also see PerSeptive Biosystems Product Literature). As a general reference for PNA synthesis methodology see Nielsen et al., Peptide Nucleic Acids; Protocols and Applications, Horizon Scientific Press, Norfolk England (1999).

Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that is condensed with the next synthon to be added to the growing polymer.

PNA may be synthesized at any scale, from submicromole to millimole, or more. PNA can be conveniently synthesized at the 2 μmole scale, using Fmoc(Bhoc) protecting group monomers on an Expedite Synthesizer (Applied Biosystems) using a XAL, PAL or many other commercially available peptide synthesis supports. Alternatively, the Model 433A Synthesizer (Applied Biosystems) with a suitable solid support (e.g. MBHA support) can be used. Moreover, many other automated synthesizers and synthesis supports can be utilized. Synthesis can be performed using continuous flow method and/or a batch method. PNA can be manually synthesized.

Regardless of the synthetic method used, because standard peptide chemistry is utilized, natural and non-natural amino acids can be routinely incorporated into a PNA oligomer. For the purposes of the design of a hybridization probe suitable for antiparallel binding to the target sequence, the N-terminus of the probing nucleobase sequence of the PNA probe is the equivalent of the 5'-hydroxyl terminus of an equivalent DNA or RNA oligonucleotide.

The compositions described herein can be used in sequencing techniques based on the enzymatic method of Sanger et al. (Sanger et al., 1977, Proc. Natl. Acad. Sci., 74: 5463-5467). The Sanger technique uses controlled synthesis of nucleic acids to generate fragments that terminate at specific points along the sequence of interest. Techniques based on the Sanger method typically begin by annealing a synthetic sequencing primer to a single-stranded nucleic acid template. Depending on the labeling strategy used to identify the bases, one or four separate reactions can be set up. For example, if the template is DNA, and no label is used, four different sequencing reactions are set up each containing a polymerase and four dNTP precursors (i.e., dGTP, dCTP, DATP and dTTP). The four reactions also contain a small proportion of a terminator, such as 2',3'-ddNTP that carries a 3'-H atom on the deoxyribose moiety, rather than the conventional 3'-OH group. Incorporation of a terminator molecule into the growing DNA chain prevents formation of a phosphodiester bond with the succeeding dNTP, thus, further extension of the growimg chain is impossible. Wne products of the reaction are a population of oligonucleotide chains whose lengths are determined by the distance between the 5' terminus of the primer used to initiate DNA synthesis and the sites of chain termination. These populations of oligonucleotides can be separated by electrophoresis and the sequence of the template DNA determined. See, e.g., U.S. Pat. Nos. 5,332,666; 5,821,058; 6,258,568; 5,800,996, 5,863,727; 5,945,526; 5,498,523; and 4,994,372; Sanger, et al., 1972, Proc. Natl. Acad. Sci., 74: 5463-5467; and Sanger, 1981, Science, 214: 1205-1210.

To improve detection of the differently sized primer extension products, various labeling strategies can be used. For example, in the embodiment illustrated in FIG. 2, "labeled primer sequencing" is used. In labeled primer sequencing, a detectable label, denoted by an asterisk (*), is incorporated onto primer 12. Generally, the detectable label will be attached at the 5' terminus of primer 12. In the embodiment illustrated in FIG. 2, primer 12 is extended in the presence of template polynucleotide 8 comprising priming sequence 14, sequence of interest 10, blocking sequence 18 and blocking probe 16. Four separate extension/termination reactions are run in parallel, each extension reaction containing a different terminator, i.e., ddTTP, ddATP, ddGTP, and ddCTP, a polymerase, four dNTP precursors (i.e., dGTP, dCTP, dATP and dTTP), and an appropriate buffer. The products of the reactions illustrated in FIG. 2 are a population of differently sized oligonucleotide chains whose lengths are determined by the distance between the 5' terminus of primer 12 used to initiate DNA synthesis, the sites of chain termination via incorporation of one of the four terminators, and location of duplex 24, formed between blocking sequence 18 and blocking probe 16.

In other embodiments, different primers are used in the four separate extension/termination reactions, each primer containing a different spectrally resolvable label. After termination, the reaction products from the four extension/termination reactions can be pooled, electrophoretically separated and detected in a single lane. See, for example, Smith et al., 1986, Nature, 321: 674-679.

Figure 3:
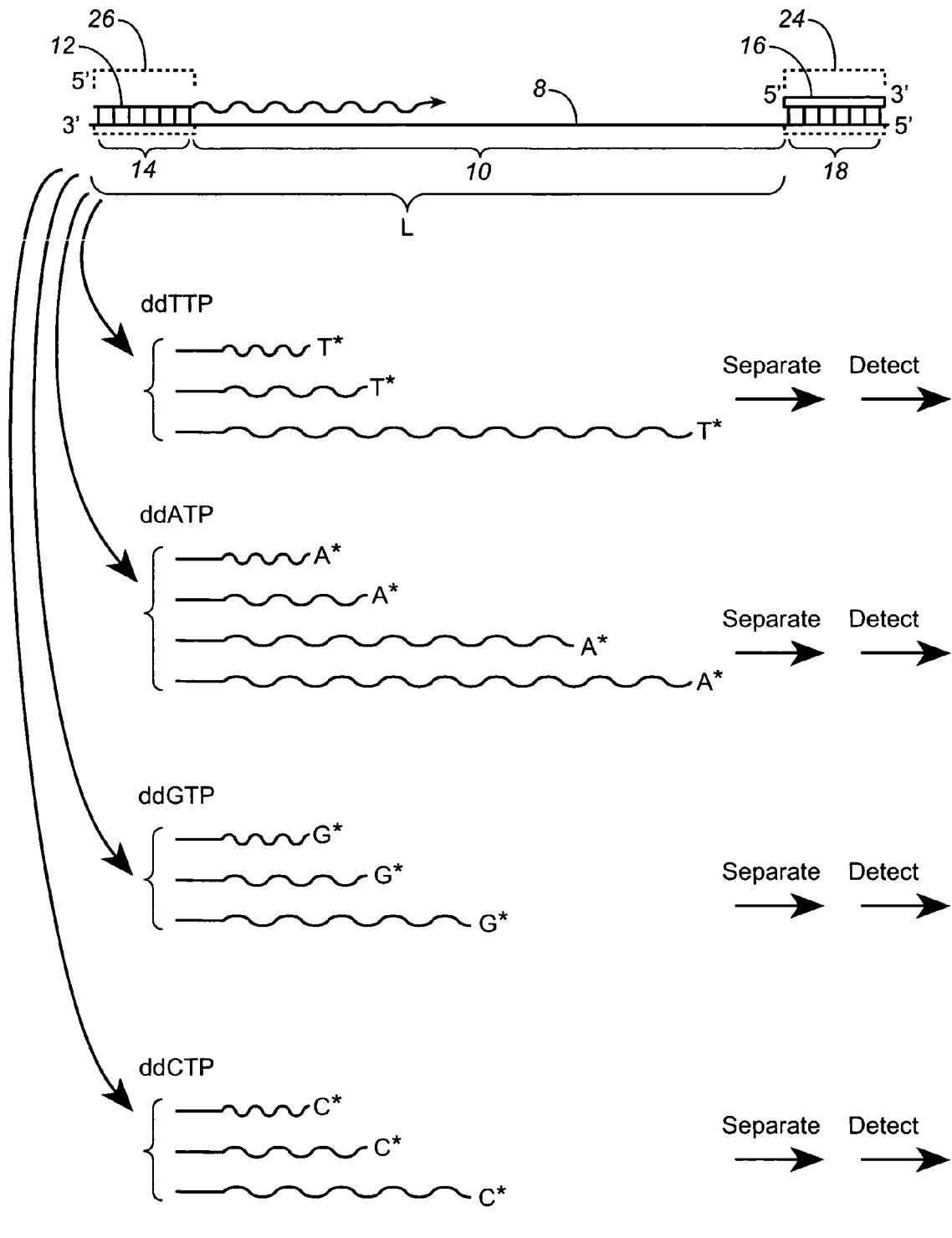
FIG. 3 illustrates an embodiment of a sequencing reaction utilizing labeled terminators (e.g., dideoxynucleotides (ddNTPs))

In other embodiments, labeled terminator sequencing is used. In the embodiment illustrated in FIG. 3, a detectable label, denoted by an asterisk (*), is attached to each of the terminators. Primer extension is initiated upon binding of primer 12 to priming sequence 14 located on template polynucleotide 8. In addition to priming sequence 12, template polynucleotide 8 comprises sequence of interest 10, blocking sequence 18 and blocking probe 16. In the embodiment illustrated in FIG. 3, four separate extension/termination reactions are run in parallel, each extension reaction containing a different terminator, i.e., ddTTP, ddATP, ddGTP, and ddCTP, a polymerase, four dNTP precursors (i.e., dGTP, dCTP, dATP and dTTP), and an appropriate buffer. The terminators can be labeled with the same detectable label or each ddNTP can be labeled with a different, spectrally resolvable detectable label. The products of the reactions illustrated in FIG. 3 are a population of differently sized oligonucleotide chains comprising a labeled terminator. The lengths of the differently sized oligonucleotide chains are determined by the distance between the 5' terminus of primer 12 used to initiate DNA synthesis, the sites of chain termination via incorporation of one of the four terminators, and location of duplex 24, formed between blocking sequence 18 and blocking probe 16. Once terminated, the reaction products for each terminator are separated and detected.

Figure 4:
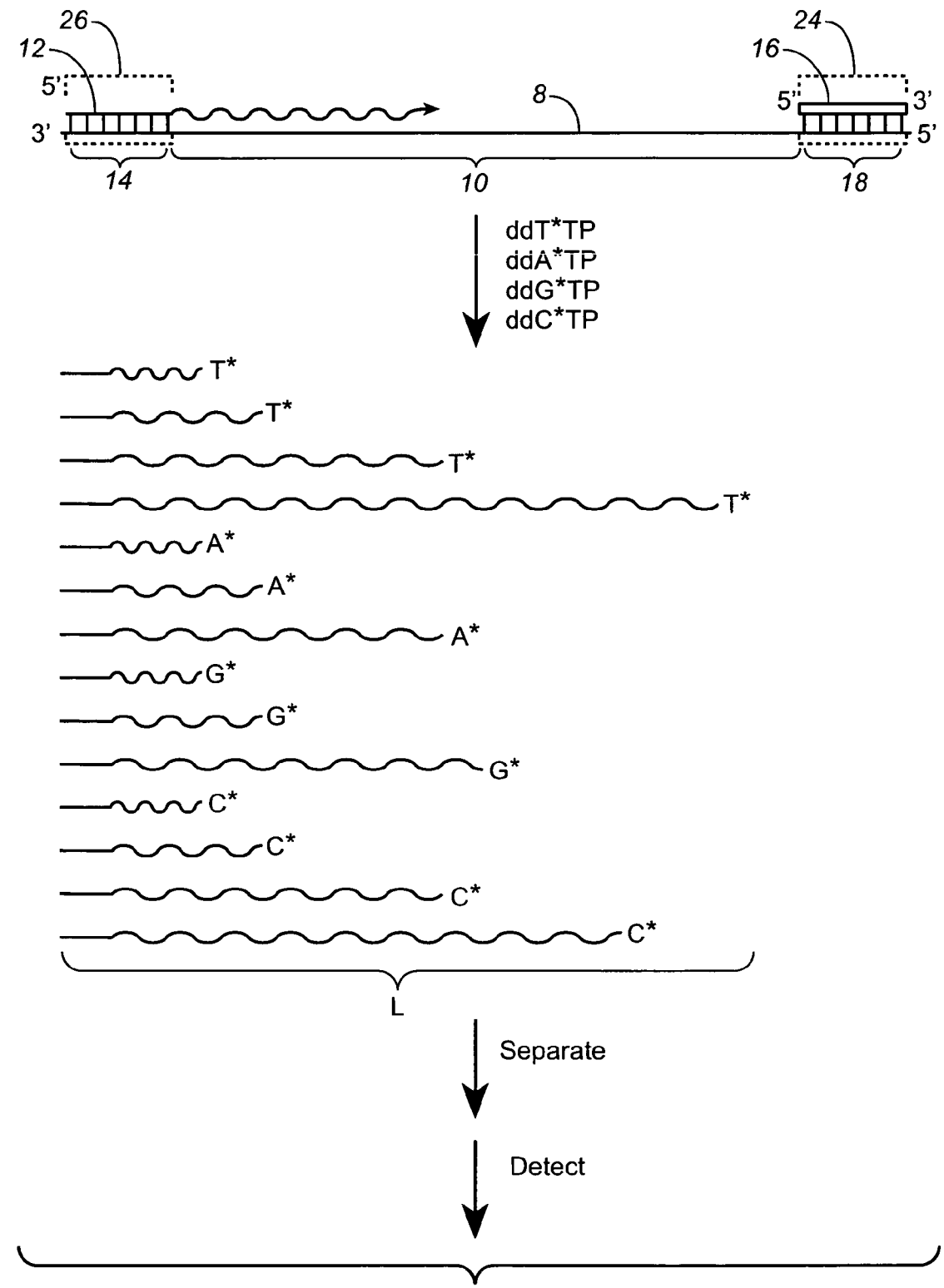
FIG. 4 illustrates an embodiment of a sequencing reaction utilizing differently labeled ddNTPs.

In the embodiment illustrated in FIG. 4, a single extension/termination reaction can be used which contains the four dideoxynucleoside triphosphates, each labeled with a different, spectrally resolvable label, denoted by the symbols *, ●, ▲, and ■. Suitable spectrally resolvable labels include, but are not limited to, fluorophores. See, for example, U.S. Pat. Nos. 5,821,058, 5,332,666 and 5,945,526.

Figure 5:
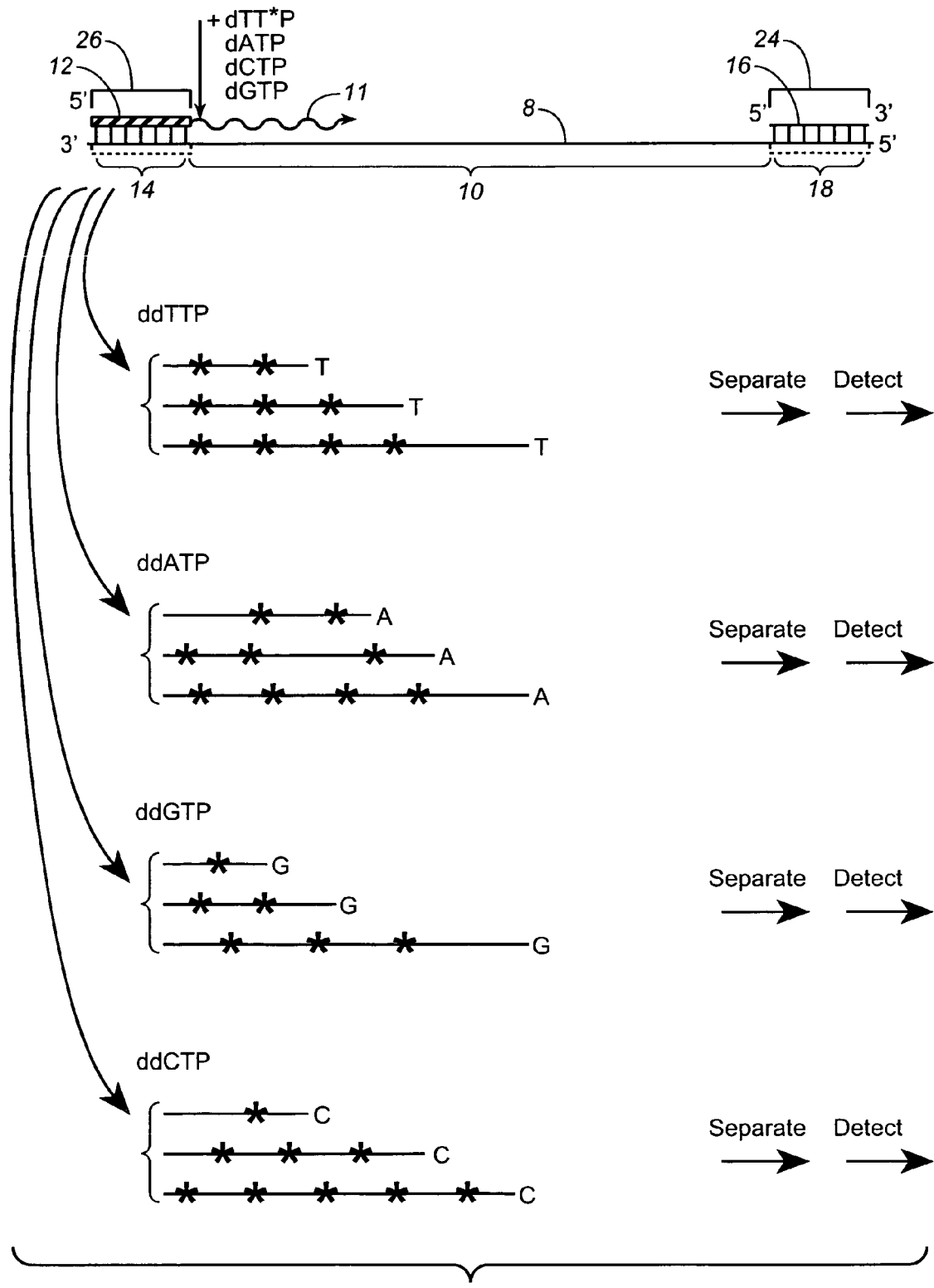
FIG. 5 illustrates an embodiment of a sequencing reaction utilizing labeled deoxynucleotides (dNTPs)

In the embodiment illustrated in FIG. 5, a detectable label, denoted by an asterisk (*), is attached to one of the dNTPs. In embodiments using a labeled dNTP, four separate extension/termination reactions are conducted in the presence of a mixture comprising a specific terminator, e.g., ddTTP, a low concentration of the corresponding deoxynucleoside triphosphate, e.g., dTTP, and normal concentrations of the other three deoxynucleoside triphosphates, one of which is labeled with a detectable label. The detectable label can be a radioisotope or any other suitable moiety that permits detection of the labeled primer extension products, including, but not limited to, fluorophores. Four separate primer extension/termination reactions are conducted as described above to generate a population of labeled primer extension products. Once terminated, the reaction products for each terminator are separated and detected.

A variety of nucleic acid polymerases may be used in the methods described herein. For example, the nucleic acid polymerizing enzyme can be a thermostable polymerase or a thermally degradable polymerase. Suitable thermostable polymerases include, but are not limited to, polymerases isolated from *Thermus aquaticus, Thermus thermophilus, Pyrococcus woesei, Pyrococcusfuriosus, Thermococcus litoralis,* and *Thermotoga maritima*. Suitable thermodegradable polymerases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include T7, T3, SP6 RNA polymerases and AMV, M-MLV and HIV reverse transcriptases.

Non-limiting examples of commercially available polymerases that can be used in the methods described herein include, but are not limited to, TaqFS®, AmpliTaq CS (Perkin-Elmer), AmpliTaq FS (Perkin-Elmer), Kentaql (AB Peptide, St. Louis, Mo.), Taquenase (ScienTech Corp., St. Louis, Mo.), ThermoSequenase (Amersham), Bst polymerase, Vent$_R$(exo$^-$) DNA polymerase, Reader™ Taq DNA polymerase, VENT™ DNA polymerase (New England Biolabs), DEEPVENT™ DNA polymerase (New England Biolabs), PFU-Turbo™ DNA polymerase (Stratagene), Tth DNA polymerase, KlenTaq-1 polymerase, SEQUENASE™ 1.0 DNA polymerase (Amersham Biosciences), and SEQUENASE 2.0 DNA polymerase (United States Biochemicals).

In some embodiments, a sequencing reaction(s) can be carried out in the presence of one or more thermostable polymerases.

The concentrations of the template polynucleotide, polymerase, dNTPs, sequencing primer, terminators, blocking probe, and other reagents are not critical to the success of the disclosed methods provided they are present in sufficient concentrations to allow the sequence of the sequence of interest to be determined. Guidance for selecting the appropriate concentrations of the various reagents used in the sequencing reaction(s) can be found for example, in Sambrook and Russell, 2001, *Molecular Cloning: A Laboratory Manual,* 3$^{rd}$ Edition, Chapter 12, Cold Spring Harbor Laboratory Press. Suitable concentrations for the polymerase can range from about 0.01 units/μl to about 10 units/μl. Suitable concentrations for the sequencing primer can range from about 0.05 μM to about 50 μM. The concentration of each chain-elongating nucleotide (e.g., dNTPs) can be in the range of about 1 μM to about 10 mM at the start of the primer extension process. Suitable concentrations for the terminators can be in the range of about 10 n-M each to about 100 μM each. The template polynucleotide can be present at any suitable concentration, e.g., in the range of about 1 ng/μl to about 10 μg/μl.

Suitable concentrations for the blocking probe can be determined empirically, for example, by titration. For a selected template polynucleotide, the concentration of the blocking probe can be selected relative to the concentration of template polynucleotide so as to minimize the generation of run-on fragments. In some embodiments, the initial molar ratio of blocking probe to template polynucleotide is approximately 2:1, (e.g., 2 pmole$_{blocking\ probe}$: 1 pmole$_{template}$). In other embodiments, the molar ratio is approximately 10:1. In other embodiments, the molar ratio is approximately 1:1. As will be appreciated by a person skilled in the art, other molar ratios can be used provided that that the generation of primer extension products beyond the site where the blocking probe binds is reduced or prevented.

The reaction mixture(s) can additionally include an appropriate buffering system to maintain a constant pH, divalent, and monovalent cations (such as MgCl$_2$ and KCl). Other components that can be added include reducing agents and detergents that can be used to enhance the reaction rate or fidelity of the sequencing reaction(s).

In some embodiments, commercially available sequencing kits can be purchased and used with the disclosed compositions. For example, both the blocking probe and the template polynucleotide comprising the blocking sequence and/or the priming sequence can be prepared as recommended by the kit manufacturer and added to the reaction mixture comprising the various components of the kit. Suitable kits include, but are not limited to, BigDye® Terminator Cycle Sequencing Kits (Applied Biosystems).

The duration of a sequencing reaction or reactions will depend, in part, upon the length of the region being sequenced, upon the amount of product desired, and upon the polymerase selected. Representative reactions for conventional sequencing reactions are exemplified in Ansorge, W., Voss, H., and Zimmermann. J., eds., 1996, *DNA Sequencing Strategies*, Wiley-Liss.

The instant methods can be used in conjunction with low temperature isothermal nucleic acid sequencing, or with cycle sequencing (see, e.g., U.S. Pat. Nos. 6,376,183, 6,043,059, 5,998,143, 5,756,285, 5,741,676, 5,741,640, 5,723,298, 5,675,679, 5,423,065, and Sambrook and Russell, 2001, *Molecular Cloning: A Laboratory Manual*, 3$^{rd}$ Edition, Chapter 12, Cold Spring Harbor Laboratory Press). For example, a sequencing reaction can be cycled through various temperatures for a selected number of cycles. In some embodiments, a thermal sequencing reaction can be carried out for 25 cycles using the following thermal sequence: 95° C., 10 seconds; 50° C., 5 seconds; 60° C., 4 minutes. In some embodiments, a sequencing reaction can be carried out for 20 cycles using the following thermal sequence: 20 seconds at 95° C., 20 seconds at 55° C., 20 seconds at 72° C. Thus, any combination of temperatures and cycles can be used with the methods described herein, provided that primer extension products can be generated and detected. Any conventional temperature control system can be used for this purpose, such as any one of the ABI Prism® Instruments, e.g., ABI Prism® 3700 DNA Analyzer, ABI Prism® Genetic Analyzer, ABI Prism® 377 DNA Sequencer (Applied Biosystems).

In other embodiments, the instant methods can be used in conjunction with bisulfite sequencing reactions for the methylation analysis of genomes (see, e.g., Grunau, et. al., Nucleic Acids Research, 29: e65).

Although the type of label is not critical to success, the labels used should produce detectable signals. Suitable labels include radioisotopes, fluorescent dyes, chromophores, spin labels, raman dyes, enzyme labels, infrared labels, and chemiluminescent labels. Certain of these labels require covalent attachment which can be accomplished using any one of a large number of known techniques employing known labels, linkages, linking groups, reagents, reaction conditions, analysis and purification methods. When attaching a label that requires a linkage, for example, the linkage linking the label and primer, the label should not (i) interfere with primer extension, (ii) inhibit polymerase activity or (iii) adversely affect the detectable property of the label. Sequencing primers can be obtained commercially or labeled by linking a fluorogenic molecule to the 5' terminus of the primer (see, e.g., U.S. Pat. Nos. 5,538,848 and 6,573,047).

In some embodiments, the detectable label is a fluorescent dye. Guidance for selecting appropriate fluorescent dyes can be found in Smith et al., 1987, Meth. Enzymol. 155:260-301, Karger et al., 1991, Nucl. Acids Res. 19:4955-4962; Haugland, 1989, Handbook of Fluorescent Probes and Research Chemicals (Molecular Probes, Inc., Eugene, Oreg.). Suitable fluorescent dyes include xanthene, fluorescein and derivatives thereof (such as disclosed in U.S. Pat. Nos. 4,318,846 and 6,316,230, and by Lee et al., 1989, Cytometry 10:151-164), rhodamine, cyanine, phthalocyanine, squaraine, and bodipy dyes. Examples of specific fluorescent dyes include, but are not limited to, 6-FAM, JOE, TAMA, ROX, HEX-1, HEX-2, ZOE, TET-1, NAN-2, 5- and 6-carboxyfluorescein, 5- and 6-carboxy-4,7-dichlorofluorscein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein (see, e.g., U.S. Pat. Nos. 4,997,928; 4,855,225; and 5,188,934). For examples of primers labeled with spectrally resolvable rhodamine dyes see U.S. Pat. No. 5,366,860.

In some embodiments, the detectable label comprises a fluorescent energy transfer dye (see, e.g., U.S. Pat. Nos. 5,800,996, 5,863,727 and 5,945,526; Lee et al., Nucleic Acids Research, 25 (14): 2816-2822 (1997)).

In other embodiments, the detectable label is a radioisotope. Non-limiting examples of radioisotopes suitable for use in the method and kit embodiments described herein include $^{32}$P, $^{33}$P, $^{35}$S.

The products of the sequencing reaction can be analyzed by a wide variety of methods. For example, the products can be separated by a size-dependent process, e.g., gel electrophoresis, capillary electrophoresis or chromatography, thin layer chromatography, or paper chromatography. The separated fragments can be detected, e.g., by laser-induced fluorescence (see, e.g., U.S. Pat. Nos. 5,945,526; 5,863,727; 5,821,058; 5,800,996; 5,332,666; 5,633,129; and 6,395,486), autoradiography, or chemiluminescence. In some embodiments, the products of the sequencing reaction can be separated using gel electrophoresis and visualized using stains such as ethidium bromide or silver stain. The reaction products can also be analyzed by mass spectrometric methods (see, e.g., U.S. Pat. Nos. 6,225,450 and 5,210,412).

In some embodiments, the reaction products can be separated and analyzed by capillary electrophoresis (see, e.g., U.S. Pat. Nos. RE37,941, 5,384,024, 6,372,106, 6,372,484, 6,387,234, 6,387,236, 6,402,918, 6,402,919, 6,432,651, 6,462,816, 6,475,361, 6,476,118, 6,485,626, 6,531,041, 6,544,396, 6,576,105, 6,592,733, 6,596,140, 6,613,212, 6,635,164, and 6,706,162).

In embodiments in which the maximum length of the primer extension products for a given sequencing reaction is determined using a blocking probe, a capillary electrophoresis method can be used that lacks a flush cycle. A flush cycle typically comprises a set of parameters selected by the operator which are used to flush the capillary to remove any traces of old sample or contamination and to equilibrate the capillary with the run buffer (see, e.g., U.S. Pat. No. 5,384,024). Depending on the instrument, parameters that can be set to control the flush cycle include capillary fill volume, pre-run voltage and/or polarity, pre-run time, flush time, oven temperature, vial position for the autosampler, vacuum level, and detector wavelength. Elimination of the flush cycle reduces the overall time required to run a sample by at least one minute, by at least two minutes, by at least three minutes, by at least five minutes, by at least seven minutes, by at least ten minutes, by at least twelve minutes, by at least fifteen minutes, and by at least twenty minutes.

In some embodiments, the existing data collection software used by commercially available capillary electrophoresis instruments can be modified to eliminate the flush cycle. For example, the flush cycle for the Applied Biosystems 3100 Genetic Analyzer Sequencing and GeneScan modules can be controlled by selecting from a range of pre-stored values for the "cap fill volume," "pre run voltage," and "pre run time" parameters. For example, for the separation of a 500 base pair fragment, the flush cycle runs for approximately thirteen minutes, and includes a "cap fill volume" of 184 steps, requiring approximately 10 minutes, a "pre run voltage" of 15 kV and a pre run time of 180 seconds. Although the stored values for the "cap fill volume" and "pre run time" cannot be set to zero, values that approximate zero can be set. For example, a value of at least one, of at least two, of at least three, of at least four, of at least five, of at least seven, and of at least ten steps can be selected for the "cap fill volume." A value of at least one, at least two, and at least five seconds can be selected for the "pre run time." In some embodiments, a value of one can be selected for both the "cap fill volume" and the "pre-run time," and a value of zero for the "pre run voltage."

In some embodiments, a software program can be written and used with existing instruments. An exemplary example of one such program for use with the Applied Biosystems 3100 Genetic Analyzer is illustrated in FIG. 10. As illustrated in FIG. 10, the "cap fill volume," "pre run voltage," and "pre run time" parameters have been eliminated from the Sequencing and GeneScan Modules.

It is to be understood that software programs for other capillary electrophoresis instruments, such as Applied Biosytems 3130 Genetic Analyzer, Agilent's Capillary Electrophoresis system, and Beckman Coulter's P/ACE™ MDQ series capillary electrophoresis systems, can be analogously modified and/or new software programs written to generate capillary electrophoresis methods lacking a flush cycle as described herein, and thus, the methods are not limited to the specific embodiments disclosed herein.

By eliminating the flush cycle, multiple samples can be injected and analyzed using a single capillary. In these embodiments, each sample to be analyzed comprises a population of primer extension products within a selected size range that have been generated using a blocking probe in the sequencing reaction mixture. The maximum length of the primer extension products in each sample can be the same or different. The number of samples that can be injected, separated, and analyzed, depends in part, upon the nature of the material comprising the capillary tube and the presence or absence of a polymer coating. For example, using an Applied Biosystems silica capillary tube dynamically coated with a polymer, between 2 to 8 samples can be injected sequentially. In other embodiments, between 5 to 10 samples can be injected sequentially. In yet other embodiments, between 10 to 20 samples can be injected sequentially. In another example, Beckman silica capillary tubes coated with a polymer can also be injected sequentially using the methods described herein.

5.3 Kits

The compositions and reagents described herein can be packaged into kits. In some embodiments, the kit comprises a blocking probe. The blocking probe can be specifically designed or comprise a universal sequence (see, supra). In some embodiments, the blocking probe can be used in conjunction with commercially available sequencing kits, including, but not limited to, those available from Applied Biosystems (i.e., Big Dye® Terminator Cycle Sequencing Kit), Epicentre (i.e., SequiTherm™ Cycle Sequencing Kit), Amersham (i.e., DYEnamic Direct Dye-Primer Cycle Sequencing Kits), Boehringer Mannheim (i.e., CycleReader™ DNA Sequencing Kit), Bionexus Inc. (i.e., AccuPower DNA Sequencing Kit), and USB cycle sequencing kits (i.e., Thermo Sequenase™ Cycle Sequencing Kit).

In other embodiments, the blocking probe is included in a kit. The various components included in the kit are typically contained in separate containers, however, in some embodiments, one or more of the components can be present in the same container. Additionally, kits can comprise any combination of the compositions and reagents described herein. For example, in some embodiments, the kit can comprise a blocking probe and a mixture of different terminators, e.g., ddATP, ddTTP, ddGTP, ddCTP, or ddUTP, each of which terminates a template-dependent primer extension reaction at a different template nucleotide. Additionally, each terminator can comprise a label, such as a fluorescent label. In some embodiments, the different terminating nucleotides comprise a fluorescent label capable of producing a detectable, spectrally resolvable fluorescent signal.

In other embodiments, kits can comprise a blocking probe, terminators, and dNTPs, i.e., ATP, GTP, CTP, TTP or UTP. In some embodiments, one or more of the dNTPs can be detectably labeled, for example with a radioisotope.

In other embodiments, kits can comprise a blocking probe, terminators, dNTPs, and a sequencing primer that can optionally be labeled with a detectable label. Kits can further comprise a polymerase, such as a DNA or an RNA polymerase.

In other embodiments, kits can comprise a vector that can be used in carrying out the disclosed methods. A wide variety of vectors can be used for preparing polynucleotide templates for sequencing by the compositions and methods described herein. Suitable vectors include commercially available vectors, such as yeast artificial chromosome vectors (YAC), bacterial artificial chromosome vectors (BAC), phage artificial chromosome vectors, cosmids, plasmids, phagemids, and M13 vectors (see, e.g., Sambrook and Russell, 2001, *Molecular Cloning: A Laboratory Manual*, Chapter 1, $3^{rd}$ ed., Cold Spring Harbor Laboratory Press, and Ausubel et al., eds., 1996, *Current Protocols in Molecular Biology*, John Wiley & Sons, pp. 7.1.2-7.1.6). A vector can comprise a polylinker comprising restriction sites for insertion of a sequence of interest. The ability to insert a sequence of interest into a vector is within the capabilities of a person skilled in the art (see, e.g., Sambrook and Russell, 2001, *Molecular Cloning: A Laboratory Manual*, Chapters 1-4, $3^{rd}$ ed., Cold Spring Harbor Laboratory Press). After insertion of a sequence of interest (in either a forward or reverse direction), the cloning vector can be subjected to clonal amplification, and a single stranded template obtained for use as the template polynucleotide according to the methods disclosed herein.

In some embodiments, the cloned template polynucleotide comprises, in a 3'→5' direction, a priming sequence, the sequence of interest and a blocking sequence. For example, in the embodiment illustrated in FIG. 6A, polynucleotide 60 (FIG. 6A) comprises one strand of a cloning vector comprising an insert 62. Insert 62 comprises, in a 3'→5' direction, a priming sequence 64, a sequence of interest 66 and a blocking sequence 68.

In other embodiments, a vector suitable for use in the compositions and methods described herein can be constructed from various combinations of polynucleotide fragments using conventional methods. In some embodiments, the vector can be constructed by modifying existing vectors. In other embodiments, the vector can be constructed de novo. Vectors so constructed can comprise a priming sequence and/or a blocking sequence. In addition, the vector can comprise other sequences, such as a polylinker that can be used to clone additional sequences selected by the user. For example, the polylinker could be used to insert a blocking sequence or a priming sequence adjacent to the sequence of interest. Moreover, the number of bases separating the blocking sequence from the sequence of interest can be chosen by the user, depending in part, on the location of the polylinker, and the restriction site within the polylinker used to clone the blocking sequence.

Figure 6A:
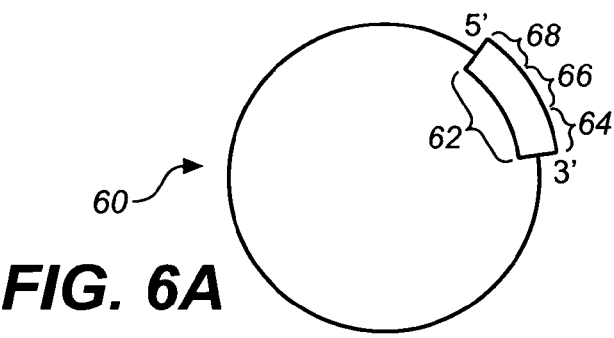
Figure 6B:
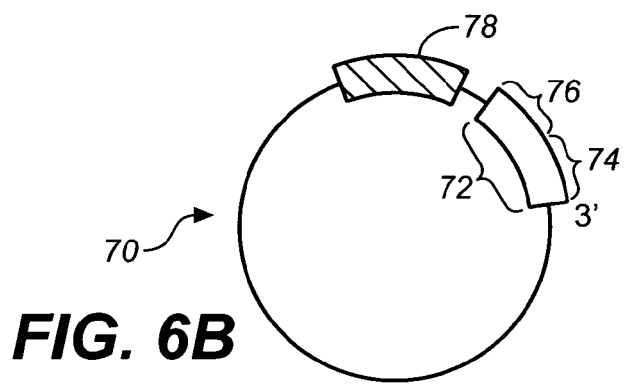

In the embodiment illustrated in FIG. 6B, polynucleotide 70 represents one strand of a cloning vector comprising insert 72, and blocking sequence 78. Insert 72 comprises priming sequence 74 and sequence of interest 76. In some embodiments, blocking sequence 78 comprises a universal sequence. In other embodiments, blocking sequence 78 is a specifically designed sequence. In some embodiments, polynucleotide 70 comprises a modification of a known vector. In other embodiments, polynucleotide 70 comprises a de novo constructed vector.

Figure 6C:
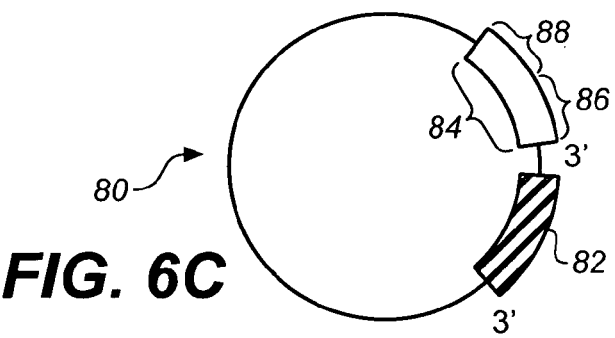

In some embodiments, a cloning vector can be constructed as illustrated in FIG. 6C. Polynucleotide 80 represents one strand of a cloning vector comprising priming sequence 82, and modified by insertion of sequence 84. Insert 84 comprises sequence of interest 86 and blocking sequence 88. Blocking sequence 88 can comprise a universal sequence or be specifically designed. Polynucleotide 80 can comprise a modification of a known vector, or comprise a de novo constructed vector.

Figure 6D:
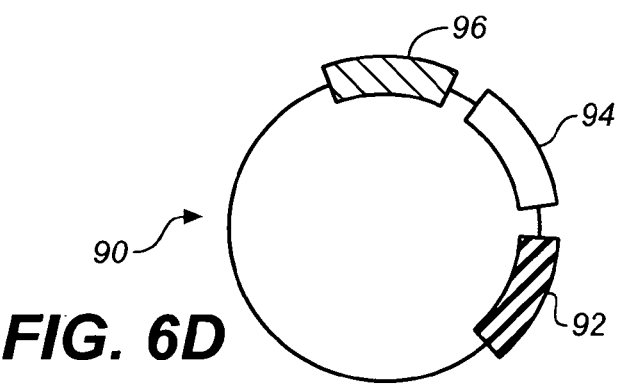

In some embodiments, a cloning vector can be constructed as illustrated in FIG. 6D. Polynucleotide 90 represents one strand of a cloning vector comprising blocking sequence 96, and priming sequence 92. The blocking sequence can be a universal sequence or a specifically designed sequence. Similarly, the priming sequence can be a universal sequence or a specifically designed sequence. Polynucleotide 90 can comprise a modification of a known vector, or comprise a de novo constructed vector. Additionally, the vector illustrated in FIG. 6D can be modified by insert 94 comprising a sequence of interest.

In addition to the compositions and reagents described herein, the kits can comprise amplification primers for adding a blocking sequence and/or a priming sequence to a sequence of interest (see, supra). For example, the kit can comprise a polymerase, a forward amplification primer, and a first reverse amplification primer, wherein said forward amplification comprises a 5' tail sequence complementary to a sequencing primer and said first reverse amplification comprises a sequence complementary to the sequence of interest, a second reverse amplification primer, wherein said second reverse amplification primer comprises a 5' tail sequence complementary to a blocking probe, and a blocking probe as described herein.

The kits described herein can comprise additional reagents that are necessary for performing the disclosed methods. Such reagents include, but are not limited to, buffers, molecular size standards, and control polynucleotide templates.

All literature and similar materials cited in this application, including but not limited to patents, patent applications, articles, books, and treatises, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

All numerical ranges in this specification are intended to be inclusive of their upper and lower limits.

Unless defined otherwise, all technical and scientific terms used herein have the same meaning as commonly understood by one of ordinary skill in the art to which this invention belongs. Unless mentioned otherwise the techniques employed or contemplated herein are standard methodologies well known to one of ordinary skill in the art. The materials, methods and examples are illustrative only and not limiting.

6. EXAMPLES

6.1 Use of Blocking Probes to Reduce or Eliminate the Generation of Primer Extension Products in Sequencing Reactions A sequencing reaction comprising linearized DNA as the template, primer, terminator, enzyme, dNTPs and a terminator, e.g., ddNTPs was performed as recommended by the manufacturer (Applied Biosystems, Big Dye® Terminator Cycle Sequencing). Unreacted terminator was removed and the product was analyzed on the ABI3100 Genetic Analyzer.

As depicted in FIG. 7, small uncut DNA peaks can be detected after the last predetermined fragment peak of 600 bases due to incomplete linearization digestion.

In contrast, blocking probe PNA3 was included in a sequencing reaction mixture comprising a circular DNA template, primer, terminator, enzyme, dNTPs and ddNTPs. The reaction was preformed as described above. Unreacted terminator was removed and the product was analyzed on the ABI3100 Genetic Analyzer.

As depicted in FIG. 8, no peak comprising primer extension products appeared after the last predetermined fragment peak of 600 bases. The absence of prinmer P.xte.nsion products after the last predetermined fragment peak is due to the inclusion of the blocking probe in the sequencing reaction.

6.2 Sequential Injection Method using Capillary Electrophoresis

A sequencing reaction including a blocking probe were performed as described above. The resulting primer extension products were injected and analyzed on an ABI3100 Genetic Analyzer according to the ABI3100 Genetic Analyzer user manual.

FIG. 9A illustrates the first injection (i.e., injection 1) of the primer extension products generated in the sequencing reaction. Numbers on each peak indicate peak width. As in FIG. 8, inclusion of a blocking probe eliminates primer extension products longer than the last predetermined fragment peak of 600 bases.

Six more injections were made after injection 1, without purging and refilling the polymer. Injections after injection 1 were performed in the same manner as the injection 1, except the capillary fill step in the run module was change to 1 second to eliminate the polymer replenishment step.

FIG. 9B illustrates the 7th injection. A comparison of peak width between FIG. 9A and FIG. 9B, shows that the peaks obtained from the first injection and the seventh injection are similar. Thus, inclusion of a blocking probe eliminated the need for the reconditioning step between successive samples.

What is claimed is:

1. A method of sequencing a nucleic acid, comprising the steps of:
  a) forming a first, second, third, and fourth reaction mixture such that:
    (i) the first reaction mixture comprises a sequencing primer and a terminating nucleotide complementary to adenosine;
    (ii) the second reaction mixture comprises a sequencing primer and a terminating nucleotide complementary to cytosine;
    (iii) the third reaction mixture comprises a sequencing primer and a terminating nucleotide complementary to guanosine; and,
    (iv) the fourth reaction mixture comprises a sequencing primer and a terminating nucleotide complementary to thymidine or uridine;
  b) combining each of the first, second, third, and fourth reaction mixtures with a template polynucleotide, a polymerase, a mixture of nucleoside triphosphates suitable for enzymatic primer extension, and at least one blocking probe, wherein said template polynucleotide comprises, in a 3' to 5' direction, a priming sequence complementary to the sequencing primer, a sequence of interest, and a blocking sequence complementary to the blocking probe;
  c) enzymatically extending the sequencing primer in the first, second, third and fourth reaction mixtures to form a plurality of differently-sized primer extension products;
  d) separating the primer extension products based upon their sizes; and
  e) determining therefrom the sequence of the sequence of interest.

2. The method according to claim 1 in which the sequencing primer comprises a detectable label such that the primer extension products are detected based upon detection of said label.

3. The method according to claim 1 in which at least one of the nucleoside triphosphates in each of the four different reaction mixtures comprises a detectable label such that the primer extension products are detected based upon detection of said label.

4. The method according to claim 1 in which the blocking probe is selected from the group consisting of a DNA, RNA, LNA, PNA and a chimera oligo.

5. The method according to claim 4 in which the blocking probe is PNA.

6. The method according to claim 1 in which the melting temperature ($T_m$) of the blocking probe is between 1° C. to 10° C. greater than the temperature at which the polymerase used in the sequencing reaction begins to extend the primer.

7. The method according to claim 1 in which said template polynucleotide is an amplicon produced by:
  a) amplifying a sequence of interest of said nucleic acid in the presence of a polymerase, a forward amplification primer, and a first reverse amplification primer, wherein said forward amplification comprises a 5' tail sequence complementary to a sequencing primer and said forward amplification primer and/or said first reverse amplification primer comprise a sequence complementary to the sequence of interest; and
  b) linearly amplifying the amplification product of step (a) in the presence of a second reverse amplification primer to form said template polynucleotide, wherein said second reverse amplification primer comprises a 5' tail sequence complementary to a blocking probe, and said template polynucleotide comprises in a 3' to 5' direction, the priming sequence, the sequence of interest and the blocking sequence.

8. A capillary electrophoretic method for rapidly sequencing two or more nucleic acid samples comprising the steps of:
  a) generating a population of primer extension products within a selected size range for a nucleic acid sample to be analyzed by forming a first, second, third, and fourth reaction mixture such that:
    (i) the first reaction mixture comprises a sequencing primer and a terminating nucleotide complementary to adenosine;
    (ii) the second reaction mixture comprises a sequencing primer and a terminating nucleotide complementary to cytosine;
    (iii) the third reaction mixture comprises a sequencing primer and a terminating nucleotide complementary to guanosine; and,
    (iv) the fourth reaction mixture comprises a sequencing primer and a terminating nucleotide complementary to thymidine or uridine;
  b) enzymatically extending the sequencing primer in the first, second, third and fourth reaction mixtures in the presence of a composition comprising a template polynucleotide, a polymerase, a mixture of nucleoside triphosphates suitable for enzymatic primer extension, and at least one blocking probe to form a plurality of differently-sized primer extension products, wherein said template polynucleotide comprises, in a 3' to 5' direction, a priming sequence complementary to the sequencing primer, a sequence of interest, and a blocking sequence complementary to the blocking probe;
  c) injecting an aliquot of the primer extension products of the sample onto a capillary;
  d) separating the primer extension products of the sample;
  e) detecting the separated primer extension products of the sample; and f) performing steps a) though e) for a second nucleic acid sample.

9. The method according to claim 8 further comprising performing steps a) through e) from 1 to 8 additional times with subsequent nucleic acid samples.

10. A method of sequencing a nucleic acid, comprising the steps of
   a) forming a reaction mixture comprising a sequencing primer and a set of four different terminating nucleotides, each of which terminates a template-dependent primer extension reaction at a different template nucleotide and comprises a fluorescent dye capable of producing a detectable, spectrally resolvable fluorescent signal;
   b) enzymatically extending the sequencing primer in the reaction mixture in the presence of a composition comprising a template polynucleotide, a polymerase, a mixture of nucleoside triphosphates suitable for enzymatic primer extension, and at least one blocking probe to form a first plurality of differently-sized fluorescently labeled primer extension products, within a selected size range, wherein said template polynucleotide comprises, in a 3' to 5' direction, a priming sequence complementary to the sequencing primer, a sequence of interest, and a blocking sequence complementary to the blocking probe;
   c) separating the plurality of differently-sized fluorescently labeled primer extension products based upon their sizes by capillary electrophoresis;
   d) detecting the fluorescently labeled extended primers based upon their spectrally resolvable fluorescent signals;
   e) determining therefrom the sequence of the sequence of interest; and
   f) performing steps a) through e) for a second nucleic acid sample, wherein the capillary is not flushed between injections of the first and second pluralities of primer extension products.

11. The method according to claim 10 further comprising performing steps a) through e) from 1 to 8 additional times with subsequent nucleic acid samples.

12. A method for terminating a sequencing reaction, comprising the steps of:
   a) forming a reaction mixture comprising a sequencing primer and at least one terminating nucleotide;
   b) enzymatically extending the sequencing primer in the reaction mixture in the presence of a composition comprising a template polynucleotide, a polymerase, a mixture of nucleoside triphosphates suitable for enzymatic primer extension, wherein the sequencing primer, the terminator(s), or one or more of the nucleoside triphosphates comprises a detectable label;
   c) terminating the primer extension products at a pre-determined location on said template polynucleotide using at least one blocking probe, wherein said template polynucleotide comprises, in a 3' to 5' direction, a priming sequence complementary to the sequencing primer, a sequence of interest, and a blocking sequence complementary to the blocking probe; and
   d) separating the labeled primer extension products by injecting said products onto a capillary, wherein the capillary is not flushed between sequential injections of said primer extension products.

* * * * *